United States Patent
Yang et al.

(10) Patent No.: US 11,278,633 B2
(45) Date of Patent: Mar. 22, 2022

(54) DUMMY-FLUORESCENT PROTEIN FUSIONS AND METHODS OF USE

(71) Applicant: MASSACHUSETTS INSTITUTE OF TECHNOLOGY, Cambridge, MA (US)

(72) Inventors: Aimei Yang, Cambridge, MA (US); Demian Park, Cambridge, MA (US); Kiryl Piatkevich, Cambridge, MA (US); Edward Boyden, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/318,428

(22) PCT Filed: Jul. 20, 2017

(86) PCT No.: PCT/US2017/043065
§ 371 (c)(1),
(2) Date: Jan. 17, 2019

(87) PCT Pub. No.: WO2018/017831
PCT Pub. Date: Jan. 25, 2018

(65) Prior Publication Data
US 2019/0290786 A1    Sep. 26, 2019

Related U.S. Application Data

(60) Provisional application No. 62/365,068, filed on Jul. 21, 2016.

(51) Int. Cl.
*A61K 49/00* (2006.01)
*C12N 15/85* (2006.01)

(52) U.S. Cl.
CPC .......... *A61K 49/0045* (2013.01); *C12N 15/85* (2013.01); *C07K 2319/60* (2013.01)

(58) Field of Classification Search
None
See application file for complete search history.

(56) References Cited

U.S. PATENT DOCUMENTS

2010/0227400 A1* 9/2010 Campbell ............ G01N 33/585
  435/367
2013/0333073 A1* 12/2013 Siegel .................. A01C 14/00
  800/298

FOREIGN PATENT DOCUMENTS

WO       2013/071231 A1      5/2013

OTHER PUBLICATIONS

Shaner et al., "A guide to choosing fluorescent proteins," Nature Methods 2:905-909 (2005) (Year: 2005).*

Bakayan, A., et al., "Red Fluorescent Protein-Aequorin Fusions as Improved Bioluminescent Ca2+ Reporters in Single Cells and Mice." PLOS One, vol. 6, No. 5, May 11, 2011, p. e19520.
Chow, B.Y., et al., "High-performance genetically targetable optical neural silencing by light-driven proton pumps." Nature vol. 463, 98-102 (2010).
Christensen, A.H., et al., "Ubiquitin promoter-based vectors for high-level expression of selectable and/or screenable marker genes in monocotyledonous plants." Transgenic Research, 5, pp. 213-218(1996).
Day, R.N & Davidson M.W., "The fluorescent protein palette: tools for cellular imaging." Chem Soc. Rev. Oct. 2009 ; 38(10): 2887-2921. doi: 10.1039/b901966a.
Gradinaru, V. et al., "eNpHR: a Natronomonas halorhodopsin enhanced for optogenetic applications." Brain Cell Biology vol. 36, 129-139, 2008.
International Preliminary Report on Patentability and the Written Opinion of the International Search Authority dated Jan. 31, 2019 from corresponding International Application No. PCT/US2017/043065 filed n Jul. 20, 2017.
International Search Report dated Oct. 24, 2017 from corresponding International Application No. PCT/US2017/043065 filed on Jul. 20, 2017.
Knopfel, T., et al., "Toward the Second Generation of Optogenetic Tools." Journal of Neuroscience, vol. 30, No. 45, Nov. 10, 2010, p. 14998-15004.
Miyawaki, A, et al., "Red fluorescent proteins: chromophore formation and cellular applications." Current Opinion in Structural Biology vol. 22, Issue 5, Oct. 2012, pp. 679-688.
Zhang, F., et al., "Multimodal fast optical interrogation of neural circuitry." Nature MacMillan Journals Ltd., etc., vol. 446, No. 7136, Apr. 5, 2007, pp. 633-639.
Chow, X. et al., "High-performance genetically targetable optical neural silencing by light-driven proton pumps." Nature 463, 98-102 (2010).
Gradinaru, V. et al., "eNpHR: a Natronomonas halorhodopsin enhanced for optogenetic applications." Cell Biol. 36, 129-139(2008).
Klapoetke et al. "Independent optical excitation of distinct neural populations." (2014) Nature Methods 11(3), 338-346.
Kügler, S. et al., "Human synapsin 1 gene promoter confers highly neuron-specific long-term transgene expression from an adenoviral vector in the adult rat brain depending on the transduced area." Gene Therapy 10, 337-347, (2003).
Yizhar, O. et al. "Optogenetics in Neural Systems." (2011) Neuron vol. 71:9-34.

* cited by examiner

*Primary Examiner* — Julie Ha
*Assistant Examiner* — Kristina M Hellman
(74) *Attorney, Agent, or Firm* — Pierce Atwood LLP

(57) ABSTRACT

The invention, in some aspects, relates to dummy-fluorescent (DF) polypeptide molecules and their encoding nucleic acid molecules and use of such molecules in fusion proteins and their encoding nucleic acid molecules. Compositions of the invention may be delivered to cells and subjects and used in methods to modulate electrical activity of cells in which they are expressed, and for treatment of diseases and conditions in subjects.

13 Claims, 8 Drawing Sheets

Specification includes a Sequence Listing.

DM1 td Tomato channel 2 ul AAV-Syn-ChrimsonR-td DM1
28 days after 500x 250x 20x td

DM2 td Tomato channel 2 ul AAV-Syn-ChrimsonR-td DM2
28 days after 500x 250x 20x td

Wild type tdTomato td Tomato channel 2 ul AAV-Syn-ChrimsonR-td
28 days after 500x 250x 20x td GFP channel (anti-RFP)

2 ul AAV-Syn-ChrimsonR-td DM1
28 days after 500x 250x 20x GFP

GFP channel (anti-RFP)

2 ul AAV-Syn-ChrimsonR-td DM2
28 days after 500x 250x 20x GFP

GFP channel (anti-RFP)

2 ul AAV-Syn-ChrimsonR-td
28 days after 500x 250x 20x GFP pAAV-Syn-Chrimson R-Td-Tomato 0.24 mW/mm²
10.43 mW/mm²
1.11 mW/mm² pAAV-Syn-Chrimson R-Td-Tomato-Dummy 1

0.24 mW/mm²
10.43 mW/mm²
1.11 mW/mm² pAAV-Syn-Chrimson R-td-Tomato-Dummy 2

| # | | |
|---|---|---|
| 1 | pAAV-Syn-ChrimsonR-tdTomato | R-tdT |
| 2 | pAAV-Syn-ChrimsonR | R |
| 3 | pAAV-Syn-ChrimsonR-HA | R-HA |
| 4 | pAAV-Syn-ChrimsonR-SS-ER2 | SS- R-ER2 |
| 5 | pAAV-Syn-ChrimsonR-SS-ER2-HA | SS- R-ER2-HA |
| 6 | pAAV-Syn-SS-CsChrimsonR-ER2-HA | SS-Cs R-ER2-HA |
| 7 | pAAV-Syn-ChrimsonR-tdTomato-DM1 | Dummy 1 |
| 8 | pAAV-Syn-ChrimsonR-tdTomato-DM2 | Dummy 2 |

| Peak pA/pF, 1.11 mW/ mm² | | | | | | |
|---|---|---|---|---|---|---|
| | R-tdT | R | R-HA | SS- R-ER2 | SS- R-ER2-HA | SS-Cs R-ER2-HA | Dummy 1 | Dummy 2 |
| AVG | -6.12 | -0.53 | -0.68 | -1.77 | -1.95 | -0.57 | -6.40 | -4.86 |
| SEM | 0.97 | 0.25 | 0.30 | 1.21 | 1.05 | 0.08 | 1.36 | 1.06 |
| n | 6 | 3 | 3 | 3 | 4 | 3 | 4 | 4 |

| Peak pA/pF, 10.43 mW/ mm² | | | | | | |
|---|---|---|---|---|---|---|
| | R-tdTomato | R | R-HA | SS- R-ER2 | SS- R-ER2-HA | SS-Cs R-ER2-HA | Dummy 1 | Dummy 2 |
| AVG | -5.98 | -0.66 | -0.86 | -2.28 | -2.28 | -0.49 | -6.28 | -4.77 |
| SEM | 0.91 | 0.32 | 0.40 | 1.41 | 1.29 | 0.04 | 1.49 | 1.13 |
| n | 6 | 3 | 3 | 3 | 4 | 3 | 4 | 4 |
| # | 1 | 2 | 3 | 4 | 5 | 6 | 7 | 8 |

Fig. 5C

SEQUENCE LISTING

```
<160> NUMBER OF SEQ ID NOS: 19

<210> SEQ ID NO 1
<211> LENGTH: 476
<212> TYPE: PRT
<213> ORGANISM: Artificial Sequence
<220> FEATURE:
<223> OTHER INFORMATION: Synthetic Polypeptide

<400> SEQUENCE: 1

Met Val Ser Lys Gly Glu Glu Val Ile Lys Glu Phe Met Arg Phe Lys
1               5                   10                  15

Val Arg Met Glu Gly Ser Met Asn Gly His Glu Phe Glu Ile Glu Gly
            20                  25                  30
```

```
Glu Gly Glu Gly Arg Pro Tyr Glu Gly Thr Gln Thr Ala Lys Leu Lys
            35                  40                  45

Val Thr Lys Gly Gly Pro Leu Pro Phe Ala Trp Asp Ile Leu Ser Pro
 50                  55                  60

Gln Phe Met Tyr Gly Ser Lys Ala Tyr Val Lys His Pro Ala Asp Ile
 65                  70                  75                  80

Pro Asp Tyr Lys Lys Leu Ser Phe Pro Glu Gly Phe Lys Trp Glu Arg
                 85                  90                  95

Val Met Asn Phe Glu Asp Gly Gly Leu Val Thr Val Thr Gln Asp Ser
                100                 105                 110

Ser Leu Gln Asp Gly Thr Leu Ile Tyr Lys Val Lys Met Arg Gly Thr
            115                 120                 125

Asn Phe Pro Pro Asp Gly Pro Val Met Gln Lys Lys Thr Met Gly Trp
            130                 135                 140

Glu Ala Ser Thr Glu Arg Leu Tyr Pro Arg Asp Gly Val Leu Lys Gly
145                 150                 155                 160

Glu Ile His Gln Ala Leu Lys Leu Lys Asp Gly Gly His Tyr Leu Val
                165                 170                 175

Glu Phe Lys Thr Ile Tyr Met Ala Lys Lys Pro Val Gln Leu Pro Gly
            180                 185                 190

Tyr Tyr Tyr Val Asp Thr Lys Leu Asp Ile Thr Ser His Asn Glu Asp
            195                 200                 205

Tyr Thr Ile Val Glu Gln Tyr Glu Arg Ser Glu Gly Arg His His Leu
            210                 215                 220

Phe Leu Gly His Gly Thr Gly Ser Thr Gly Ser Gly Ser Ser Gly Thr
225                 230                 235                 240

Ala Ser Ser Glu Asp Asn Asn Met Ala Val Ile Lys Glu Phe Met Arg
                245                 250                 255

Phe Lys Val Arg Met Glu Gly Ser Met Asn Gly His Glu Phe Glu Ile
            260                 265                 270

Glu Gly Glu Gly Glu Gly Arg Pro Tyr Glu Gly Thr Gln Thr Ala Lys
            275                 280                 285

Leu Lys Val Thr Lys Gly Gly Pro Leu Pro Phe Ala Trp Asp Ile Leu
            290                 295                 300

Ser Pro Gln Phe Met Tyr Gly Ser Lys Ala Tyr Val Lys His Pro Ala
305                 310                 315                 320

Asp Ile Pro Asp Tyr Lys Lys Leu Ser Phe Pro Glu Gly Phe Lys Trp
                325                 330                 335

Glu Arg Val Met Asn Phe Glu Asp Gly Gly Leu Val Thr Val Thr Gln
            340                 345                 350

Asp Ser Ser Leu Gln Asp Gly Thr Leu Ile Tyr Lys Val Lys Met Arg
            355                 360                 365

Gly Thr Asn Phe Pro Pro Asp Gly Pro Val Met Gln Lys Lys Thr Met
            370                 375                 380

Gly Trp Glu Ala Ser Thr Glu Arg Leu Tyr Pro Arg Asp Gly Val Leu
385                 390                 395                 400

Lys Gly Glu Ile His Gln Ala Leu Lys Leu Lys Asp Gly Gly His Tyr
                405                 410                 415

Leu Val Glu Phe Lys Thr Ile Tyr Met Ala Lys Lys Pro Val Gln Leu
            420                 425                 430

Pro Gly Tyr Tyr Tyr Val Asp Thr Lys Leu Asp Ile Thr Ser His Asn
            435                 440                 445
```

Glu Asp Tyr Thr Ile Val Glu Gln Tyr Glu Arg Ser Glu Gly Arg His
    450                 455                 460

His Leu Phe Leu Tyr Gly Met Asp Glu Leu Tyr Lys
465                 470                 475

<210> SEQ ID NO 2
<211> LENGTH: 1431
<212> TYPE: DNA
<213> ORGANISM: Artificial Sequence
<220> FEATURE:
<223> OTHER INFORMATION: Synthetic Polynucleotide

<400> SEQUENCE: 2

| | | | | | |
|---|---|---|---|---|---|
| atggtgagta | agggcgagga | agtgatcaaa | gagttcatgc | ggtttaaggt | gagaatggaa | 60 |
| ggaagcatga | acggccacga | gttcgaaatt | gagggagaag | gagagggacg | gccctacgag | 120 |
| ggcacccaga | cagccaagct | gaaagtgaca | aagggcgggc | tctgccatt | cgcttgggac | 180 |
| atcctgagcc | acagtttat | gtacggctcc | aaggcctatg | tgaaacatcc | agctgacatt | 240 |
| cccgattata | agaaactgag | cttccccgag | gggtttaagt | gggaaagagt | gatgaacttc | 300 |
| gaggacggag | gcctggtgac | tgtgacccag | gacagctccc | tgcaggatgg | gaccctgatc | 360 |
| tacaaggtga | aaatgagagg | gacaaatttt | cccctgatg | gacctgtgat | gcagaagaaa | 420 |
| actatgggat | gggaggcctc | caccgaaagg | ctgtatccac | gcgacggggt | gctgaaagga | 480 |
| gaaatccacc | aggctctgaa | gctgaaagat | ggggacatt | acctggtgga | gttcaagaca | 540 |
| atctacatgg | ccaagaaacc | tgtgcagctg | ccaggctact | attacgtgga | cacaaaactg | 600 |
| gatatcactt | cacacaacga | ggactacact | attgtggagc | agtatgaacg | agcgaggggg | 660 |
| agacaccatc | tgttcctggg | ccatgggact | ggaagtaccg | gctcagggtc | tagtggaacc | 720 |
| gcctcaagcg | aggataacaa | tatggctgtg | atcaaagagt | tcatgaggtt | taaggtgcgc | 780 |
| atggagggca | gcatgaatgg | gcacgaattt | gagattgaag | agagggcga | agggaggcct | 840 |
| tacgagggca | cacagactgc | caagctgaaa | gtgaccaagg | gaggaccact | gcctttcgct | 900 |
| tgggatatcc | tgtctcctca | gtttatgtac | ggaagtaagg | cctatgtcaa | gcatcccgct | 960 |
| gacattcctg | attacaagaa | actgtctttc | ccagagggct | taagtggga | gagagtgatg | 1020 |
| aattttgaag | atggaggcct | ggtgaccgtg | acacaggact | cctctctgca | ggatggcact | 1080 |
| ctgatctaca | aagtcaaaat | gcgcggcacc | aattttccac | ccgatgggcc | cgtgatgcag | 1140 |
| aagaaaacaa | tggggtggga | ggccagcact | gaacggctgt | atcctagaga | cggagtgctg | 1200 |
| aagggcgaaa | tccaccaggc | cctgaagctg | aaagacggcg | ccactacct | ggtggagttc | 1260 |
| aaaaccatct | acatggccaa | gaaaccagtg | cagctgcccg | gctattacta | tgtggacacc | 1320 |
| aagctggata | tcacatccca | caatgaagac | tacaccattg | tggaacagta | tgagaggtct | 1380 |
| gaaggacgcc | accatctgtt | tctgtacggc | atggatgagc | tgtataagta | a | 1431 |

<210> SEQ ID NO 3
<211> LENGTH: 476
<212> TYPE: PRT
<213> ORGANISM: Artificial Sequence
<220> FEATURE:
<223> OTHER INFORMATION: Synthetic Polypeptide

<400> SEQUENCE: 3

Met Val Ser Lys Gly Glu Glu Val Ile Lys Glu Phe Met Arg Phe Lys
1               5                   10                  15

Val Arg Met Glu Gly Ser Met Asn Gly His Glu Phe Glu Ile Glu Gly
            20                  25                  30

```
Glu Gly Glu Gly Arg Pro Tyr Glu Gly Thr Gln Thr Ala Lys Leu Lys
            35                  40                  45

Val Thr Lys Gly Gly Pro Leu Pro Phe Ala Trp Asp Ile Leu Ser Pro
 50                  55                  60

Gln Phe Met Ala Gly Ser Lys Ala Tyr Val Lys His Pro Ala Asp Ile
 65                  70                  75                  80

Pro Asp Tyr Lys Lys Leu Ser Phe Pro Glu Gly Phe Lys Trp Glu Arg
                 85                  90                  95

Val Met Asn Phe Glu Asp Gly Gly Leu Val Thr Val Thr Gln Asp Ser
                100                 105                 110

Ser Leu Gln Asp Gly Thr Leu Ile Tyr Lys Val Lys Met Arg Gly Thr
            115                 120                 125

Asn Phe Pro Pro Asp Gly Pro Val Met Gln Lys Lys Thr Met Gly Trp
            130                 135                 140

Glu Ala Ser Thr Glu Arg Leu Tyr Pro Arg Asp Gly Val Leu Lys Gly
145                 150                 155                 160

Glu Ile His Gln Ala Leu Lys Leu Lys Asp Gly Gly His Tyr Leu Val
                165                 170                 175

Glu Phe Lys Thr Ile Tyr Met Ala Lys Lys Pro Val Gln Leu Pro Gly
            180                 185                 190

Tyr Tyr Tyr Val Asp Thr Lys Leu Asp Ile Thr Ser His Asn Glu Asp
            195                 200                 205

Tyr Thr Ile Val Glu Gln Tyr Glu Arg Ser Glu Gly Arg His His Leu
210                 215                 220

Phe Leu Gly His Gly Thr Gly Ser Thr Gly Ser Gly Ser Ser Gly Thr
225                 230                 235                 240

Ala Ser Ser Glu Asp Asn Asn Met Ala Val Ile Lys Glu Phe Met Arg
                245                 250                 255

Phe Lys Val Arg Met Glu Gly Ser Met Asn Gly His Glu Phe Glu Ile
            260                 265                 270

Glu Gly Glu Gly Glu Gly Arg Pro Tyr Glu Gly Thr Gln Thr Ala Lys
            275                 280                 285

Leu Lys Val Thr Lys Gly Gly Pro Leu Pro Phe Ala Trp Asp Ile Leu
        290                 295                 300

Ser Pro Gln Phe Met Ala Gly Ser Lys Ala Tyr Val Lys His Pro Ala
305                 310                 315                 320

Asp Ile Pro Asp Tyr Lys Lys Leu Ser Phe Pro Glu Gly Phe Lys Trp
                325                 330                 335

Glu Arg Val Met Asn Phe Glu Asp Gly Gly Leu Val Thr Val Thr Gln
            340                 345                 350

Asp Ser Ser Leu Gln Asp Gly Thr Leu Ile Tyr Lys Val Lys Met Arg
        355                 360                 365

Gly Thr Asn Phe Pro Pro Asp Gly Pro Val Met Gln Lys Lys Thr Met
370                 375                 380

Gly Trp Glu Ala Ser Thr Glu Arg Leu Tyr Pro Arg Asp Gly Val Leu
385                 390                 395                 400

Lys Gly Glu Ile His Gln Ala Leu Lys Leu Lys Asp Gly Gly His Tyr
                405                 410                 415

Leu Val Glu Phe Lys Thr Ile Tyr Met Ala Lys Lys Pro Val Gln Leu
            420                 425                 430

Pro Gly Tyr Tyr Tyr Val Asp Thr Lys Leu Asp Ile Thr Ser His Asn
        435                 440                 445
```

Glu Asp Tyr Thr Ile Val Glu Gln Tyr Glu Arg Ser Glu Gly Arg His
    450                 455                 460

His Leu Phe Leu Tyr Gly Met Asp Glu Leu Tyr Lys
465                 470                 475

<210> SEQ ID NO 4
<211> LENGTH: 1431
<212> TYPE: DNA
<213> ORGANISM: Artificial Sequence
<220> FEATURE:
<223> OTHER INFORMATION: Synthetic Polynucleotide

<400> SEQUENCE: 4

```
atggtgagta agggcgagga agtgatcaaa gagttcatgc ggtttaaggt gagaatggaa      60
ggaagcatga acggccacga gttcgaaatt gagggagaag agagggacg gccctacgag      120
ggcacccaga cagccaagct gaaagtgaca aagggcgggc tctgccatt cgcttgggac      180
atcctgagcc acagtttat ggccggctcc aaggcctatg tgaaacatcc agctgacatt      240
cccgattata agaaactgag cttccccgag gggtttaagt gggaaagagt gatgaacttc      300
gaggacggag gcctggtgac tgtgacccag gacagctccc tgcaggatgg gaccctgatc      360
tacaaggtga aatgagagg gacaaatttt ccccctgatg gacctgtgat gcagaagaaa      420
actatgggat gggaggcctc caccgaaagg ctgtatccac gcgacggggt gctgaaagga      480
gaaatccacc aggctctgaa gctgaaagat ggggacatt acctggtgga gttcaagaca      540
atctacatgg ccaagaaacc tgtgcagctg ccaggctact attacgtgga cacaaaactg      600
gatatcactt cacacaacga ggactacact attgtggagc agtatgaacg gagcgagggg      660
agacaccatc tgttcctggg ccatgggact ggaagtaccg gctcagggtc tagtggaacc      720
gcctcaagcg aggataacaa tatggctgtg atcaaagagt tcatgaggtt taaggtgcgc      780
atggagggca gcatgaatgg cacgaatttt gagattgaag gagagggcga agggaggcct      840
tacgagggca cacagactgc caagctgaaa gtgaccaagg aggaccact gcctttcgct      900
tgggatatcc tgtctcctca gtttatggcc ggaagtaagg cctatgtcaa gcatcccgct      960
gacattcctg attacaagaa actgtctttc ccagagggct taagtggga gagagtgatg      1020
aattttgaag atggaggcct ggtgaccgtg acacaggact cctctctgca ggatggcact      1080
ctgatctaca agtcaaaat gcgcggcacc aattttccac ccgatgggcc cgtgatgcag      1140
aagaaaacaa tggggtggga ggccagcact gaacggctgt atcctagaga cggagtgctg      1200
aagggcgaaa tccaccaggc cctgaagctg aaagacggcg ccactacct ggtggagttc      1260
aaaaccatct acatggccaa gaaaccagtg cagctgcccg ctattacta tgtggacacc      1320
aagctggata tcacatccca caatgaagac tacaccattg tggaacagta tgagaggtct      1380
gaaggacgcc accatctgtt tctgtacggc atggatgagc tgtataagta a              1431
```

<210> SEQ ID NO 5
<211> LENGTH: 476
<212> TYPE: PRT
<213> ORGANISM: Artificial Sequence
<220> FEATURE:
<223> OTHER INFORMATION: Synthetic Polypeptide

<400> SEQUENCE: 5

Met Val Ser Lys Gly Glu Glu Val Ile Lys Glu Phe Met Arg Phe Lys
1               5                   10                  15

Val Arg Met Glu Gly Ser Met Asn Gly His Glu Phe Glu Ile Glu Gly
            20                  25                  30

```
Glu Gly Glu Gly Arg Pro Tyr Glu Gly Thr Gln Thr Ala Lys Leu Lys
        35                  40                  45

Val Thr Lys Gly Gly Pro Leu Pro Phe Ala Trp Asp Ile Leu Ser Pro
    50                  55                  60

Gln Phe Met Gly Gly Ser Lys Ala Tyr Val Lys His Pro Ala Asp Ile
65                  70                  75                  80

Pro Asp Tyr Lys Lys Leu Ser Phe Pro Glu Gly Phe Lys Trp Glu Arg
                85                  90                  95

Val Met Asn Phe Glu Asp Gly Gly Leu Val Thr Val Thr Gln Asp Ser
                100                 105                 110

Ser Leu Gln Asp Gly Thr Leu Ile Tyr Lys Val Lys Met Arg Gly Thr
                115                 120                 125

Asn Phe Pro Pro Asp Gly Pro Val Met Gln Lys Lys Thr Met Gly Trp
                130                 135                 140

Glu Ala Ser Thr Glu Arg Leu Tyr Pro Arg Asp Gly Val Leu Lys Gly
145                 150                 155                 160

Glu Ile His Gln Ala Leu Lys Leu Lys Asp Gly Gly His Tyr Leu Val
                165                 170                 175

Glu Phe Lys Thr Ile Tyr Met Ala Lys Lys Pro Val Gln Leu Pro Gly
                180                 185                 190

Tyr Tyr Tyr Val Asp Thr Lys Leu Asp Ile Thr Ser His Asn Glu Asp
                195                 200                 205

Tyr Thr Ile Val Glu Gln Tyr Glu Arg Ser Glu Gly Arg His His Leu
                210                 215                 220

Phe Leu Gly His Gly Thr Gly Ser Thr Gly Ser Gly Ser Ser Gly Thr
225                 230                 235                 240

Ala Ser Ser Glu Asp Asn Asn Met Ala Val Ile Lys Glu Phe Met Arg
                245                 250                 255

Phe Lys Val Arg Met Glu Gly Ser Met Asn Gly His Glu Phe Glu Ile
                260                 265                 270

Glu Gly Glu Gly Glu Gly Arg Pro Tyr Glu Gly Thr Gln Thr Ala Lys
                275                 280                 285

Leu Lys Val Thr Lys Gly Gly Pro Leu Pro Phe Ala Trp Asp Ile Leu
                290                 295                 300

Ser Pro Gln Phe Met Gly Gly Ser Lys Ala Tyr Val Lys His Pro Ala
305                 310                 315                 320

Asp Ile Pro Asp Tyr Lys Lys Leu Ser Phe Pro Glu Gly Phe Lys Trp
                325                 330                 335

Glu Arg Val Met Asn Phe Glu Asp Gly Gly Leu Val Thr Val Thr Gln
                340                 345                 350

Asp Ser Ser Leu Gln Asp Gly Thr Leu Ile Tyr Lys Val Lys Met Arg
                355                 360                 365

Gly Thr Asn Phe Pro Pro Asp Gly Pro Val Met Gln Lys Lys Thr Met
                370                 375                 380

Gly Trp Glu Ala Ser Thr Glu Arg Leu Tyr Pro Arg Asp Gly Val Leu
385                 390                 395                 400

Lys Gly Glu Ile His Gln Ala Leu Lys Leu Lys Asp Gly Gly His Tyr
                405                 410                 415

Leu Val Glu Phe Lys Thr Ile Tyr Met Ala Lys Lys Pro Val Gln Leu
                420                 425                 430

Pro Gly Tyr Tyr Tyr Val Asp Thr Lys Leu Asp Ile Thr Ser His Asn
                435                 440                 445
```

Glu Asp Tyr Thr Ile Val Glu Gln Tyr Glu Arg Ser Glu Gly Arg His
450                 455                 460

His Leu Phe Leu Tyr Gly Met Asp Glu Leu Tyr Lys
465                 470                 475

<210> SEQ ID NO 6
<211> LENGTH: 1431
<212> TYPE: DNA
<213> ORGANISM: Artificial Sequence
<220> FEATURE:
<223> OTHER INFORMATION: Synthetic Polynucleotide

<400> SEQUENCE: 6

```
atggtgagta agggcgagga agtgatcaaa gagttcatgc ggtttaaggt gagaatggaa    60
ggaagcatga acggccacga gttcgaaatt gagggagaag gagagggacg gccctacgag   120
ggcacccaga cagccaagct gaaagtgaca aagggcgggc tctgccatt cgcttgggac    180
atcctgagcc cacagtttat gggcggctcc aaggcctatg tgaaacatcc agctgacatt   240
cccgattata agaaactgag cttccccgag gggtttaagt gggaaagagt gatgaacttc   300
gaggacggag gcctggtgac tgtgacccag gacagctccc tgcaggatgg gaccctgatc   360
tacaaggtga aatgagagg gacaaatttt ccccctgatg gacctgtgat gcagaagaaa   420
actatgggat gggaggcctc caccgaaagg ctgtatccac gcgacggggt gctgaaagga   480
gaaatccacc aggctctgaa gctgaaagat gggggacatt acctggtgga gttcaagaca   540
atctacatgg ccaagaaacc tgtgcagctg ccaggctact attacgtgga cacaaaactg   600
gatatcactt cacacaacga ggactacact attgtggagc agtatgaacg gagcgagggg   660
agacaccatc tgttcctggg ccatgggact ggaagtaccg gctcagggtc tagtggaacc   720
gcctcaagcg aggataacaa tatggctgtg atcaaagagt tcatgaggtt taaggtgcgc   780
atggaggca gcatgaatgg gcacgaattt gagattaag gagagggcga agggaggcct    840
tacgagggca cacagactgc caagctgaaa gtgaccaagg gaggaccact gccttcgct   900
tgggatatcc tgtctcctca gtttatgggc ggaagtaagg cctatgtcaa gcatcccgct   960
gacattcctg attacaagaa actgtcttc ccagagggct taagtggga gagtgatg    1020
aattttgaag atggaggcct ggtgaccgtg acacaggact cctctctgca ggatggcact  1080
ctgatctaca agtcaaaat gcgcggcacc aattttccac ccgatgggcc cgtgatgcag  1140
aagaaaacaa tgggtggga ggccagcact gaacggctgt atccagaga cggagtgctg    1200
aagggcgaaa tccaccaggc cctgaagctg aaagacggcg ccactacct ggtggagttc   1260
aaaaccatct acatggccaa gaaaccagtg cagctgcccg ctattacta tgtggacacc   1320
aagctggata tcacatccca caatgaagac tacaccattg tggaacagta tgagaggtct   1380
gaaggacgcc accatctgtt tctgtacggc atggatgagc tgtataagta a           1431
```

<210> SEQ ID NO 7
<211> LENGTH: 476
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (67)..(67)
<223> OTHER INFORMATION: Amino acid can be M, G, or A
<220> FEATURE:
<221> NAME/KEY: MISC_FEATURE
<222> LOCATION: (68)..(68)

```
<223> OTHER INFORMATION: Amino acid can be Y, I, V, L, M, S, T, C, G, or
      A
<220> FEATURE:
<221> NAME/KEY: MISC_FEATURE
<222> LOCATION: (69)..(69)
<223> OTHER INFORMATION: Amino acid can be G, A, or S
<220> FEATURE:
<221> NAME/KEY: MISC_FEATURE
<222> LOCATION: (309)..(309)
<223> OTHER INFORMATION: Amino acid can be M, G, or A
<220> FEATURE:
<221> NAME/KEY: MISC_FEATURE
<222> LOCATION: (310)..(310)
<223> OTHER INFORMATION: Amino acid can be Y, I, V, L, M, S, T, C, G, or
      A
<220> FEATURE:
<221> NAME/KEY: MISC_FEATURE
<222> LOCATION: (311)..(311)
<223> OTHER INFORMATION: Amino acid can be G, A, or S

<400> SEQUENCE: 7

Met Val Ser Lys Gly Glu Glu Val Ile Lys Glu Phe Met Arg Phe Lys
1               5                   10                  15

Val Arg Met Glu Gly Ser Met Asn Gly His Glu Phe Glu Ile Glu Gly
            20                  25                  30

Glu Gly Glu Gly Arg Pro Tyr Glu Gly Thr Gln Thr Ala Lys Leu Lys
        35                  40                  45

Val Thr Lys Gly Gly Pro Leu Pro Phe Ala Trp Asp Ile Leu Ser Pro
    50                  55                  60

Gln Phe Xaa Xaa Xaa Ser Lys Ala Tyr Val Lys His Pro Ala Asp Ile
65                  70                  75                  80

Pro Asp Tyr Lys Lys Leu Ser Phe Pro Glu Gly Phe Lys Trp Glu Arg
                85                  90                  95

Val Met Asn Phe Glu Asp Gly Gly Leu Val Thr Val Thr Gln Asp Ser
            100                 105                 110

Ser Leu Gln Asp Gly Thr Leu Ile Tyr Lys Val Lys Met Arg Gly Thr
        115                 120                 125

Asn Phe Pro Pro Asp Gly Pro Val Met Gln Lys Lys Thr Met Gly Trp
130                 135                 140

Glu Ala Ser Thr Glu Arg Leu Tyr Pro Arg Asp Gly Val Leu Lys Gly
145                 150                 155                 160

Glu Ile His Gln Ala Leu Lys Leu Lys Asp Gly Gly His Tyr Leu Val
                165                 170                 175

Glu Phe Lys Thr Ile Tyr Met Ala Lys Lys Pro Val Gln Leu Pro Gly
            180                 185                 190

Tyr Tyr Tyr Val Asp Thr Lys Leu Asp Ile Thr Ser His Asn Glu Asp
        195                 200                 205

Tyr Thr Ile Val Glu Gln Tyr Glu Arg Ser Gly Arg His His Leu
210                 215                 220

Phe Leu Gly His Gly Thr Gly Ser Thr Gly Ser Gly Ser Ser Gly Thr
225                 230                 235                 240

Ala Ser Ser Glu Asp Asn Asn Met Ala Val Ile Lys Glu Phe Met Arg
                245                 250                 255

Phe Lys Val Arg Met Glu Gly Ser Met Asn Gly His Glu Phe Glu Ile
            260                 265                 270

Glu Gly Glu Gly Glu Gly Arg Pro Tyr Glu Gly Thr Gln Thr Ala Lys
        275                 280                 285

Leu Lys Val Thr Lys Gly Gly Pro Leu Pro Phe Ala Trp Asp Ile Leu
    290                 295                 300
```

```
Ser Pro Gln Phe Xaa Xaa Xaa Ser Lys Ala Tyr Val Lys His Pro Ala
305                 310                 315                 320

Asp Ile Pro Asp Tyr Lys Lys Leu Ser Phe Pro Glu Gly Phe Lys Trp
            325                 330                 335

Glu Arg Val Met Asn Phe Glu Asp Gly Gly Leu Val Thr Val Thr Gln
        340                 345                 350

Asp Ser Ser Leu Gln Asp Gly Thr Leu Ile Tyr Lys Val Lys Met Arg
    355                 360                 365

Gly Thr Asn Phe Pro Pro Asp Gly Pro Val Met Gln Lys Lys Thr Met
370                 375                 380

Gly Trp Glu Ala Ser Thr Glu Arg Leu Tyr Pro Arg Asp Gly Val Leu
385                 390                 395                 400

Lys Gly Glu Ile His Gln Ala Leu Lys Leu Lys Asp Gly Gly His Tyr
                405                 410                 415

Leu Val Glu Phe Lys Thr Ile Tyr Met Ala Lys Lys Pro Val Gln Leu
            420                 425                 430

Pro Gly Tyr Tyr Tyr Val Asp Thr Lys Leu Asp Ile Thr Ser His Asn
        435                 440                 445

Glu Asp Tyr Thr Ile Val Glu Gln Tyr Glu Arg Ser Glu Gly Arg His
    450                 455                 460

His Leu Phe Leu Tyr Gly Met Asp Glu Leu Tyr Lys
465                 470                 475

<210> SEQ ID NO 8
<211> LENGTH: 350
<212> TYPE: PRT
<213> ORGANISM: Artificial Sequence
<220> FEATURE:
<223> OTHER INFORMATION: Synthetic Polypeptide

<400> SEQUENCE: 8

Met Ala Glu Leu Ile Ser Ser Ala Thr Arg Ser Leu Phe Ala Ala Gly
1               5                   10                  15

Gly Ile Asn Pro Trp Pro Asn Pro Tyr His His Glu Asp Met Gly Cys
            20                  25                  30

Gly Gly Met Thr Pro Thr Gly Glu Cys Phe Ser Thr Glu Trp Trp Cys
        35                  40                  45

Asp Pro Ser Tyr Gly Leu Ser Asp Ala Gly Tyr Gly Tyr Cys Phe Val
    50                  55                  60

Glu Ala Thr Gly Gly Tyr Leu Val Val Gly Val Glu Lys Lys Gln Ala
65                  70                  75                  80

Trp Leu His Ser Arg Gly Thr Pro Gly Glu Lys Ile Gly Ala Gln Val
                85                  90                  95

Cys Gln Trp Ile Ala Phe Ser Ile Ala Ile Ala Leu Leu Thr Phe Tyr
            100                 105                 110

Gly Phe Ser Ala Trp Lys Ala Thr Cys Gly Trp Glu Glu Val Tyr Val
        115                 120                 125

Cys Cys Val Glu Val Leu Phe Val Thr Leu Glu Ile Phe Lys Glu Phe
    130                 135                 140

Ser Ser Pro Ala Thr Val Tyr Leu Ser Thr Gly Asn His Ala Tyr Cys
145                 150                 155                 160

Leu Arg Tyr Phe Glu Trp Leu Leu Ser Cys Pro Val Ile Leu Ile Arg
                165                 170                 175

Leu Ser Asn Leu Ser Gly Leu Lys Asn Asp Tyr Ser Lys Arg Thr Met
            180                 185                 190
```

```
Gly Leu Ile Val Ser Cys Val Gly Met Ile Val Phe Gly Met Ala Ala
            195                 200                 205

Gly Leu Ala Thr Asp Trp Leu Lys Trp Leu Leu Tyr Ile Val Ser Cys
    210                 215                 220

Ile Tyr Gly Gly Tyr Met Tyr Phe Gln Ala Ala Lys Cys Tyr Val Glu
225                 230                 235                 240

Ala Asn His Ser Val Pro Lys Gly His Cys Arg Met Val Val Lys Leu
                245                 250                 255

Met Ala Tyr Ala Tyr Phe Ala Ser Trp Gly Ser Tyr Pro Ile Leu Trp
            260                 265                 270

Ala Val Gly Pro Glu Gly Leu Leu Lys Leu Ser Pro Tyr Ala Asn Ser
    275                 280                 285

Ile Gly His Ser Ile Cys Asp Ile Ile Ala Lys Glu Phe Trp Thr Phe
290                 295                 300

Leu Ala His His Leu Arg Ile Lys Ile His Glu His Ile Leu Ile His
305                 310                 315                 320

Gly Asp Ile Arg Lys Thr Thr Lys Met Glu Ile Gly Gly Glu Glu Val
                325                 330                 335

Glu Val Glu Glu Phe Val Glu Glu Glu Asp Glu Asp Thr Val
            340                 345                 350
```

<210> SEQ ID NO 9
<211> LENGTH: 1050
<212> TYPE: DNA
<213> ORGANISM: Artificial Sequence
<220> FEATURE:
<223> OTHER INFORMATION: Synthetic Polynucleotide

<400> SEQUENCE: 9

```
atggctgagc tgatcagcag cgccaccaga tctctgtttg ccgccggagg catcaaccct      60
tggcctaacc cctaccacca cgaggacatg gctgtggag  gaatgacacc tacaggcgag     120
tgcttcagca ccgagtggtg gtgtgaccct tcttacggac tgagcgacgc cggatacgga     180
tattgcttcg tggaggccac aggcggctac ctggtcgtgg gagtggagaa gaagcaggct     240
tggctgcaca gcagaggcac accaggagaa aagatcggcg cccaggtctg ccagtggatt     300
gctttcagca tcgccatcgc cctgctgaca ttctacggct cagcgcctg gaaggccact      360
tgcggttggg aggaggtcta cgtctgttgc gtcgaggtgc tgttcgtgac cctggagatc     420
ttcaaggagt tcagcagccc cgccacagtg tacctgtcta ccggcaacca cgcctattgc     480
ctgcgctact tcgagtggct gctgtcttgc cccgtgatcc tgatcagact gagcaacctg     540
agcggcctga agaacgacta cagcaagcgg accatgggcc tgatcgtgtc ttgcgtggga     600
atgatcgtgt tcggcatggc cgcaggactg gctaccgatt ggctcaagtg gctgctgtat     660
atcgtgtctt gcatctacgg cggctacatg tacttccagg ccgccaagtg ctacgtggaa     720
gccaaccaca cgctgcctaa aggccattgc cgcatggtcg tgaagctgat ggcctacgct     780
tacttcgcct cttggggcag ctacccaatc ctctgggcag tggaccaga  aggactgctg     840
aagctgagcc cttacgccaa cagcatcggc cacagcatct gcgacatcat cgccaaggag     900
ttttggacct cctggccca  ccacctgagg atcaagatcc acgagcacat cctgatccac     960
ggcgacatcc ggaagaccac caagatggag atcggaggcg aggaggtgga agtggaagag    1020
ttcgtggagg aggaggacga ggacacagtg                                     1050
```

<210> SEQ ID NO 10
<211> LENGTH: 21

```
<212> TYPE: DNA
<213> ORGANISM: Artificial Sequence
<220> FEATURE:
<223> OTHER INFORMATION: Synthetic Polynucleotide

<400> SEQUENCE: 10
ttctgctacg agaatgaagt g                                              21

<210> SEQ ID NO 11
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 11

Phe Cys Tyr Glu Asn Glu Val
1               5

<210> SEQ ID NO 12
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 12
aaatccagaa ttacttctga aggggagtat atccctctgg atcaaataga catcaatgtt   60

<210> SEQ ID NO 13
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 13

Lys Ser Arg Ile Thr Ser Glu Gly Glu Tyr Ile Pro Leu Asp Gln Ile
1               5                   10                  15

Asp Ile Asn Val
            20

<210> SEQ ID NO 14
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 14
atggtcccgt gcacgctgct cctgctgttg gcagccgccc tggctccgac tcagacgcgg   60
gcc                                                                 63

<210> SEQ ID NO 15
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 15

Met Val Pro Cys Thr Leu Leu Leu Leu Ala Ala Ala Leu Ala Pro
1               5                   10                  15

Thr Gln Thr Arg Ala
            20
```

<210> SEQ ID NO 16
<211> LENGTH: 480
<212> TYPE: DNA
<213> ORGANISM: Artificial Sequence
<220> FEATURE:
<223> OTHER INFORMATION: Synthetic Polynucleotide

<400> SEQUENCE: 16

```
ctagactgca gagggccctg cgtatgagtg caagtgggtt ttaggaccag gatgaggcgg      60
ggtgggggtg cctacctgac gaccgacccc gacccactgg acaagcaccc aaccccatt     120 ccccaaattg cgcatcccct atcagagagg gggaggggaa acaggatgcg gcgaggcgcg    180
tgcgcactgc cagcttcagc accgcggaca gtgccttcgc ccccgcctgg cggcgcgcgc    240
caccgccgcc tcagcactga aggcgcgctg acgtcactcg ccggtccccc gcaaactccc    300
cttcccggcc accttggtcg cgtccgcgcc gccgccggcc cagccggacc gcaccacgcg    360
aggcgcgaga taggggggca cgggcgcgac catctgcgct gcggcgccgg cgactcagcg    420
ctgcctcagt ctgcggtggg cagcggagga gtcgtgtcgt gcctgagagc gcagtcgaga    480
```

<210> SEQ ID NO 17
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 17

```
tacccatacg atgttccaga ttacgct                                         27
```

<210> SEQ ID NO 18
<211> LENGTH: 9
<212> TYPE: PRT
<213> ORGANISM: Artificial Sequence
<220> FEATURE:
<223> OTHER INFORMATION: Synthetid Polypeptide

<400> SEQUENCE: 18

Tyr Pro Tyr Asp Val Pro Asp Tyr Ala
1               5

<210> SEQ ID NO 19
<211> LENGTH: 1179
<212> TYPE: DNA
<213> ORGANISM: Artificial Sequence
<220> FEATURE:
<223> OTHER INFORMATION: Synthetic Polynucleotide

<400> SEQUENCE: 19

```
gggtgcagcg gcctccgcgc cgggttttgg cgcctcccgc gggcgccccc ctcctcacgg      60
cgagcgctgc cacgtcagac gaagggcgca gcgagcgtcc tgatccttcc gcccggacgc    120
tcaggacagc ggcccgctgc tcataagact cggccttaga accccagtat cagcagaagg    180
acattttagg acgggacttg ggtgactcta gggcactggt tttctttcca gagagcggaa    240
caggcgagga aaagtagtcc cttctcggcg attctgcgga gggatctccg tggggcggtg    300
aacgccgatg attatataag gacgcgccgg gtgtggcaca gctagttccg tcgcagccgg    360
gatttgggtc gcggttcttg tttgtggatc gctgtgatcg tcacttggtg agtagcgggc    420
tgctgggctg gccggggctt tcgtggccgc cgggccgctc ggtgggacgg aagcgtgtgg    480
agagaccgcc aagggctgta gtctgggtcc gcgagcaagg ttgccctgaa ctgggggttg    540
```

```
gggggagcgc agcaaaatgg cggctgttcc cgagtcttga atggaagacg cttgtgaggc    600
gggctgtgag gtcgttgaaa caaggtgggg ggcatggtgg gcggcaagaa cccaaggtct    660
tgaggccttc gctaatgcgg gaaagctctt attcgggtga gatgggctgg ggcaccatct    720
ggggaccctg acgtgaagtt tgtcactgac tggagaactc ggtttgtcgt ctgttgcggg    780
ggcggcagtt atggcggtgc cgttgggcag tgcacccgta cctttgggag cgcgcgccct    840
cgtcgtgtcg tgacgtcacc cgttctgttg gcttataatg cagggtgggg ccacctgccg    900
gtaggtgtgc ggtaggcttt tctccgtcgc aggacgcagg gttcgggcct agggtaggct    960
ctcctgaatc gacaggcgcc ggacctctgg tgagggagg gataagtgag gcgtcagttt   1020
ctttggtcgg ttttatgtac ctatcttctt aagtagctga agctccggtt ttgaactatg   1080
cgctcggggt tggcgagtgt gttttgtgaa gttttttagg cacctttga aatgtaatca   1140 tttgggtcaa tatgtaattt tcagtgttag actagtaaa                          1179
```

DUMMY-FLUORESCENT PROTEIN FUSIONS AND METHODS OF USE

RELATED APPLICATIONS

This application is a National Stage Filing under U.S.C. § 371 of PCT International Application PCT/US2017/043065, filed Jul. 20, 2017, which claims benefit under 35 U.S.C. § 119(e) of U.S. Provisional application No. 62/365,068 filed Jul. 21, 2016, the disclosure of each of which is incorporated by reference herein in its entirety.

GOVERNMENT INTEREST

This invention was made with government support under R24-MH106075, R01-NS087950, DP2-OD002002-01, DMS-0848804, R01-DA029639-04, R01-NS075421-04, R01-DA029639-05, DPI-NS087724, and sub-award agreement no. 3024 Rehabilitation Institute of Chicago; each awarded by the National Institutes of Health. The government has certain rights in the invention.

FIELD OF THE INVENTION

The invention, in some aspects, relates to dummy-fluorescent polypeptide molecules and their encoding nucleic acid molecules and use of such molecules in fusion proteins.

BACKGROUND OF THE INVENTION

In optogenetics, some procedures include expressing a fusion protein comprising an opsin polypeptide and also a fluorescent polypeptide. The expression in a cell of a fluorescence-emitting polypeptide can result in photo bleaching and toxicity in the cell when the expressed fluorescent polypeptide is excited by contact with light. Thus, inclusion of fluorescent molecules may reduce effectiveness of optogenetic procedures and therapies.

SUMMARY OF THE INVENTION

The invention, in part, relates to molecules and compounds that can be used in optogenetic assays, diagnostic testing, and therapeutic methods. In addition, the invention in some aspects includes expression of fusion proteins comprising, a polypeptide that is a dummy-fluorescent polypeptide. For example, some aspects of the invention include use of a tandem dimer Tomato (tdTomato) polypeptide that is a dummy-fluorescent tdTomato polypeptide.

In some aspects of the invention, a fusion protein that includes a dummy-fluorescent polypeptide also includes a polypeptide that is of interest to express in a cell. In some aspects of the invention, a polypeptide of interest to express in a cell is a stimulus-activated opsin polypeptide, non-limiting examples of which are: an ion channel polypeptide and an ion pump polypeptide. In some aspects of the invention, a fusion protein may comprise one or more dummy-fluorescent polypeptides of the invention and a polypeptide of interest to express in a cell. The invention, in part, also relates to methods of treating diseases and conditions in subjects using methods that may comprise expressing at least one fusion protein in a cell in a subject, wherein the fusion protein comprises a dummy-fluorescent polypeptide and a polypeptide of interest.

According to an aspect of the invention, compositions that include a dummy-fluorescent (DF) polypeptide or DF functional variant thereof are provided. In certain embodiments, the composition also includes a stimulus-activated opsin polypeptide. In some embodiments, the opsin is a light-activated opsin polypeptide. In some embodiments, the composition is a fusion protein and comprises one or more of DF polypeptide or DF functional variant thereof and the opsin polypeptide, and optionally comprises one or more of a trafficking polypeptide and a signal polypeptide. In certain embodiments, the DF polypeptide is a DF tdTomato polypeptide. In some embodiments, the amino acid sequence of the DF polypeptide is set forth as at least one of SEQ ID NO: 3 or a DF functional variant thereof, SEQ ID NO: 5 or a DF functional variant thereof, and one of the DF polypeptides described in Table 1 or a DF functional variant thereof. In some embodiments, the composition is in a cell. In some embodiments, the cell is a vertebrate cell. In certain embodiments, the cell is a mammalian cell. In some embodiments, the cell is an excitable cell In some embodiments, the DF functional variant comprises at least one of the amino acid sequences set forth as SEQ ID NO: 3, SEQ ID NO: 5, or another of the DF polypeptides described in Table 1 having 1, 2, 3, 4, 5, 6, 7, 8, 9, 10 or more sequence modifications from the amino acid sequence of SEQ ID NO: 3, SEQ ID NO: 5, or another of the DF polypeptides described in Table 1, respectively. In certain embodiments, the amino acid sequence of the DF functional variant has at least: 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to at least one of the amino acid sequences set forth as SEQ ID NO: 3, SEQ ID NO: 5, and one of the DF polypeptides described in Table 1. In some embodiments, the opsin polypeptide is a ChrimsonR (ChR88R) polypeptide or a functional variant thereof. In some embodiments, the opsin is an opsin other than ChR88R.

According to another aspect of the invention, polynucleotides are provided that include a nucleic acid sequence encoding the DF polypeptide or DF functional variant thereof of any embodiment of the aforementioned aspect of the invention. In certain embodiments, the polynucleotide includes the sequence set forth as SEQ ID NO: 4 or a functional variant thereof. In some embodiments, the polynucleotide includes the sequence set forth as SEQ ID NO: 6 or a functional variant thereof. In certain embodiments, the nucleic acid sequence of the polynucleotide is a mammalian codon-optimized DNA sequence.

According to another aspect of the invention, vectors that include any embodiment of a polynucleotide of any aforementioned aspect of the invention are provided. In some embodiments, the polynucleotide's nucleic acid sequence is operatively linked to a promoter sequence. In some embodiments, the vector also includes one, two, or more nucleic acid signal sequences operatively linked to the nucleic acid sequence encoding an opsin polypeptide. In certain embodiments, the encoded opsin polypeptide is a ChrimsonR (ChR88R) polypeptide or a functional variant thereof. In some embodiments, the vector is a plasmid vector, cosmid vector, viral vector, or an artificial chromosome. In some embodiments, the vector also includes one or more of: a nucleic acid sequence encoding an opsin polypeptide and a nucleic acid sequence encoding a detectable label. In some embodiments, an expression product of the vector is a fusion protein comprising the DF polypeptide or a DF functional variant thereof fused to one or more of: the opsin polypeptide and the detectable label. In certain embodiments, the vector is in a cell. In some embodiments, the cell is a vertebrate cell. In some embodiments, the cell is at least one of a mammalian cell. In some embodiments, the cell is one or more of: a neuron, a neuronal cell, a central nervous system cell, a peripheral nervous system cell, a cardiac cell, a visual system cell, an auditory system cell, an immune system cell, and a muscle cell. In some embodiments, the cell is a mammalian cell. In certain embodiments, the cell is an excitable cell. In some embodiments, the amino acid sequence of the encoded DF polypeptide is the sequence set forth as at least one of: SEQ ID NO: 3 or a DF functional variant thereof, SEQ ID NO: 5 or a DF functional variant thereof, and a DF polypeptide described in Table 1 or a DF functional variant thereof.

According to another aspect of the invention, a cell that includes a vector of any embodiment of the aforementioned aspect of the invention is provided.

According to another aspect of the invention, a fusion protein that includes any embodiment of any aforementioned DF polypeptide is provided. In certain embodiments, the encoded DF polypeptide is a DF tdTomato polypeptide. In some embodiments, the DF polypeptide has the amino acid sequence of at least one of: SEQ ID NO: 3 or a DF functional variant thereof, SEQ ID NO: 5 or a DF functional variant thereof, and a DF polypeptide described in Table 1 or a DF functional variant thereof. In some embodiments, the fusion protein also comprises a stimulus-activated opsin polypeptide. In some embodiments, the stimulus-activated opsin is a light-activated opsin and the stimulus comprises one or more wavelengths of light. In certain embodiments, the encoded opsin polypeptide is a ChrimsonR (ChR88R) polypeptide or a functional variant thereof. In some embodiments, the fusion protein also comprises a detectable label. In some embodiments, the fusion protein is present in a cell. In certain embodiments, the cell is a vertebrate cell. In some embodiments, the cell is a mammalian cell. In some embodiments, the cell is an excitable cell. In some embodiments, the cell is at least one of a mammalian cell. In some embodiments, the cell is one or more of: a neuron, a neuronal cell, a central nervous system cell, a peripheral nervous system cell, a cardiac cell, a visual system cell, an auditory system cell, an immune system cell, and a muscle cell. In certain embodiments, the DF functional variant comprises at least one of: the amino acid sequence of SEQ ID NO: 3 with 1, 2, 3, 4, 5, 6, 7, 8, 9, 10, or more sequence modifications; the amino acid sequence of SEQ ID NO: 5 with 1, 2, 3, 4, 5, 6, 7, 8, 9, 10, or more sequence modifications, and the amino acid sequence of a DF polypeptide described in Table 1 with 1, 2, 3, 4, 5, 6, 7, 8, 9, 10, or more sequence modifications. In some embodiments, the amino acid sequence of the DF functional variant has at least: 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to at least one of: the amino acid sequence of SEQ ID NO: 3, SEQ ID NO: 5, and a DF polypeptide described in Table 1.

According to yet another aspect of the invention, one or more cells comprising a fusion protein of any embodiment of any aforementioned aspect of the invention is provided. In some embodiments, the cell is an in vitro, ex vivo, or in vivo cell.

According to yet another aspect of the invention, methods of modulating electrical activity in a cell are provided, the methods comprising: a) expressing in a host cell a fusion protein comprising: a dummy-fluorescent (DF) polypeptide or a DF functional variant thereof and a stimulus-activated opsin polypeptide; and b) contacting the expressed opsin polypeptide with a stimulus under suitable conditions to activate the opsin polypeptide and modulate an electrical activity in the host cell. In certain embodiments, the host cell is a vertebrate cell, optionally a mammalian cell. In some embodiments, the host cell is a human cell. In some embodiments, the host cell is a neuronal cell, a nervous system cell, a cardiac cell, a circulatory system cell, a visual system cell, or an auditory system cell. In certain embodiments, the cell is an: in vitro, ex vivo, or in vivo cell. In some embodiments, the DF functional variant comprises at least one of: the amino acid sequence of SEQ ID NO: 3 with 1, 2, 3, 4, 5, 6, 7, 8, 9, 10, or more sequence modifications and the amino acid sequence of SEQ ID NO: 5 with 1, 2, 3, 4, 5, 6, 7, 8, 9, 10, or more sequence modifications; and a DF polypeptide described in Table 1 with 1, 2, 3, 4, 5, 6, 7, 8, 9, 10, or more sequence modifications. In some embodiments, the amino acid sequence of the DF functional variant has at least: 75%, 80%, 81%, 82%, 83%, 84%, 85%, 86%, 87%, 88%, 89% 90%, 91%, 92%, 93%, 94%, 95%, 96%, 97%, 98%, or 99% sequence identity to at least one of: the amino acid sequence of SEQ ID NO: 3, SEQ ID NO: 5, and a DF polypeptide described in Table 1. In certain embodiments, the stimulus-activated opsin is a light-activated opsin and the stimulus comprises one or more wavelengths of light. In some embodiments, the amino acid sequence of the DF polypeptide is set forth as at least one of SEQ ID NO: 3 or a DF functional variant thereof, SEQ ID NO: 5 or a DF functional variant thereof, and one of the DF polypeptides described in Table 1 or a DF functional variant thereof. In certain embodiments, the stimulus-activated opsin is a ChrimsonR (ChR88R) polypeptide, or functional variant thereof.

According to another aspect of the invention, methods of treating a disease or condition in a subject are provided, the methods comprising, a) expressing in a cell of a subject in need of such treatment, a therapeutically effective amount of a fusion protein comprising a dummy-fluorescent (DF) polypeptide or a DF functional variant thereof, and a stimulus-activated opsin polypeptide, to treat the disorder; and b) contacting the opsin polypeptide expressed in the cell with a stimulus under conditions suitable to modulate an electrical activity of the cell, wherein the modulated electrical activity of the cell treats the disease or condition in the subject. In some embodiments, the disease or condition is injury, brain damage, spinal cord injury, an immune system disorder, epilepsy, cardiac dysfunction, vision loss, blindness, deafness, hearing loss, ALS, Alzheimer's disease, Parkinson's disease, seizures, or a psychiatric condition. In some embodiments, the amino acid sequence of the DF polypeptide is set forth as at least one of SEQ ID NO: 3 or a DF functional variant thereof, SEQ ID NO: 5 or a DF functional variant thereof, and one of the DF polypeptides described in Table 1 or a DF functional variant thereof. In certain embodiments, the stimulus-activated opsin is ChrimsonR (ChR88R) polypeptide, or a functional variant thereof.

According to yet another aspect of the invention, pharmaceutical compositions for delivering a stimulus-activated opsin to a cell in a subject are provided, the pharmaceutical compositions including any embodiment of a composition of any aforementioned aspect of the invention. In some embodiments, the pharmaceutical composition further comprises a pharmaceutically acceptable carrier. In some embodiments, the pharmaceutical composition also includes one or more of a: trafficking agent, targeting agent, and detectable label. In certain embodiments, the amino acid sequence of the DF polypeptide is set forth as at least one of SEQ ID NO: 3 or a DF functional variant thereof, SEQ ID NO: 5 or a DF functional variant thereof, and one of the DF polypeptides described in Table 1 or a DF functional variant thereof. In some embodiments, the stimulus-activated opsin is a ChrimsonR (ChR88R) polypeptide or a functional variant thereof.

According to another aspect of the invention, pharmaceutical compositions for delivering a stimulus-activated opsin to a cell in a subject are provided, the pharmaceutical compositions comprising any embodiment of a polynucleotide of any aforementioned aspect of the invention. In some embodiments, the pharmaceutical composition also includes a pharmaceutically acceptable carrier. In certain embodiments, the pharmaceutical composition also includes one or more nucleic acid sequences that encode a: trafficking agent polypeptide, a promoter, a targeting agent polypeptide, or a detectable label polypeptide. In some embodiments, the nucleic acid sequence encodes at least one of SEQ ID NO: 3 or a DF functional variant thereof, SEQ ID NO: 5 or a DF functional variant thereof, and one of the DF polypeptides described in Table 1 or a DF functional variant thereof. In some embodiments, the stimulus-activated opsin is a ChrimsonR (ChR88R) polypeptide or a functional variant thereof.

The present invention is not intended to be limited to a system or method that must satisfy one or more of any stated objects or features of the invention. It is also important to note that the present invention is not limited to the exemplary or primary embodiments described herein. Modifications and substitutions by one of ordinary skill in the art are considered to be within the scope of the present invention.

BRIEF DESCRIPTION OF THE DRAWINGS

FIG. 4A shows a photocurrent of a ChrimsonR-tdTomato control. FIG. 4B shows a photocurrent for a ChrimsonR-tdTomato-Dummy 1. FIG. 4C shows a photocurrent for a ChrimsonR-tdTomato-Dummy 2. pAAV-Syn-GFP was co-transfected to visualize neurons expressing ChrimsonR-tdTomato-Dummy 1 or 2.

FIG. 5A-C provides a graph and two information tables demonstrating photocurrents of ChrimsonR plasmid constructs. Photocurrent density in ChrimsonR-tdTomato-Dummy 1 (#7 in FIG. 5A and FIG. 5C) and the photocurrent density in ChrimsonR-tdTomato-Dummy 2 (#8 in FIG. 5A and FIG. 5C) were similar to ChrimsonR-tdTomato control (#1 in FIG. 5A and FIG. 5C). ChrimsonR Flurophore-Free constructs with and without trafficking signals (#2-6 in FIG. 5A and FIG. 5C) had smaller photocurrent density than the control (#1 in FIG. 5A and FIG. 5C). FIG. 5A provides a bar graph showing photocurrent density measured (AVG±SEM) in 8 different ChrimsonR plasmid constructs (#1-8) in hippocampal neurons stimulated with 640±30 nm illumination at 10.43 mW/mm$^2$ at 500 ms. FIG. 5B describes eight ChrimsonR plasmid constructs: AAV-Adeno-associated virus; Syn-synapsin; HA-hemagglutinin, SS-signal sequence, truncated MHC class I antigen corresponded to amino acid sequence (M)VPCTLLLLLAAALAPTQTRA (SEQ ID NO: 14) [Chow, X. et al., Nature 463, 98-102 (2010)], ER2—Endoplasmic reticulum export signal, FCYENEV (SEQ ID NO: 9) (C-terminus) from Kir2.1 [Gradinaru, V. et al. Brain Cell Biol. 36, 129-139 (2008)]; D1—Dummy 1, D2—Dummy 2. FIG. 5C provides photo current density measured in eight ChrimsonR plasmid constructs in response to 1.11 and 10.43 mW/mm$^2$ illumination intensity at 500 ms. Fubi-tdTomato was co-transfected to visualize neurons expressing ChrimsonR with no fluorophore (#2-6 in FIG. 5B). Photocurrent density was derived by measuring peak current (pA) using pClamp and dividing by membrane capacitance (pF).

BRIEF DESCRIPTION OF THE SEQUENCES

Figure 1:
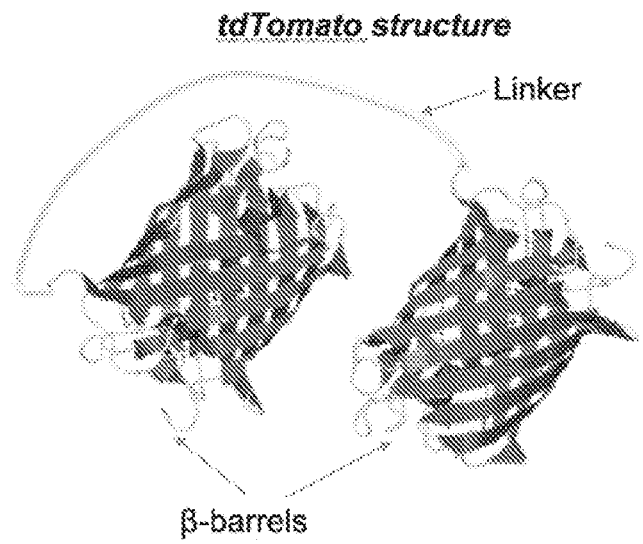
FIG. 1 is a schematic diagram showing the β-barrel architecture of the tdTomato polypeptide channel.
Figure 2:
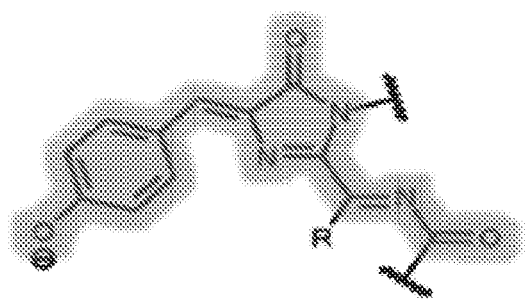
FIG. 2 shows a schematic diagram of the structure of Cis-Chromophore of tdTomato. tdTomato has the Met-Tyr-Gly chromophore-forming tripeptide.

SEQ ID NO: 1 is the amino acid sequence of tdTomato polypeptide:

```
MVSKGEEVIKEFMRFKVRMEGSMNGHEFEIEGEGEGRPYEGTQTAKLKVTK
GGPLPFAWDILSPQFMYGSKAYVKHPADIPDYKKLSFPEGFKWERVMNFED
GGLVTVTQDSSLQDGTLIYKVKMRGTNFPPDGPVMQKKTMGWEASTERLYP
RDGVLKGEIHQALKLKDGGHYLVEFKTIYMAKKPVQLPGYYYVDTKLDITS
HNEDYTIVEQYERSEGRHHLFLGHGTGSTGSGSSGTASSEDNNMAVIKEFM
RFKVRMEGSMNGHEFEIEGEGEGRPYEGTQTAKLKVTKGGPLPFAWDILSP
QFMYGSKAYVKHPADIPDYKKLSFPEGFKWERVMNFEDGGLVTVTQDSSLQ
DGTLIYKVKMRGTNFPPDGPVMQKKTMGWEASTERLYPRDGVLKGEIHQAL
KLKDGGHYLVEFKTIYMAKKPVQLPGYYYVDTKLDITSHNEDYTIVEQYER
SEGRHELFLYGMDELYK.
```

SEQ ID NO: 2 is nucleic acid sequence encoding the polypeptide set forth as SEQ ID NO: 1:

```
atggtgagtaagggcgaggaagtgatcaaagagttcatgcggtttaaggtg
agaatggaaggaagcatgaacggccacgagttcgaaattgagggagaagga
gagggacggccctacgagggcacccagacagccaagctgaaagtgacaaag
ggcgggcctctgccattcgcttgggacatcctgagcccacagtttatgtac
ggctccaaggcctatgtgaaacatccagctgacattcccgattataagaaa
ctgagcttccccgaggggtttaagtgggaaagagtgatgaacttcgaggac
ggaggcctggtgactgtgacccaggacagctccctgcaggatgggaccctg
atctacaaggtgaaaatgagagggacaaattttcccctgatggacctgtg
atgcagaagaaaactatgggatgggaggcctccaccgaaaggctgtatcca
cgcgacggggtgctgaaaggagaaatccaccaggctctgaagctgaaagat
ggggacattacctggtggagttcaagacaatctacatggccaagaaacct
gtgcagctgccaggctactattacgtggacacaaaactggatatcacttca
cacaacgaggactacactattgtggagcagtatgaacggagcgaggggaga
caccatctgttcctgggccatgggactggaagtaccggctcagggtctagt
``` ggaaccgcctcaagcgaggataacaatatggctgtgatcaaagagttcatg aggtttaaggtgcgcatggagggcagcatgaatgggcacgaatttgagatt gaaggagagggcgaagggaggccttacgagggcacacagactgccaagctg aaagtgaccaagggaggaccactgcctttcgcttgggatatcctgtctcct cagtttatgtacggaagtaaggcctatgtcaagcatcccgctgacattcct gattacaagaaactgtctttcccagagggctttaagtgggagagagtgatg aattttgaagatggaggcctggtgaccgtgacacaggactcctctctgcag gatggcactctgatctacaaagtcaaaatgcgcggcaccaattttccaccc gatgggcccgtgatgcagaagaaaacaatggggtggggaggccagcactgaa cggctgtatcctagagacggagtgctgaagggcgaaatccaccaggccctg aagctgaaagacggcggccactacctggtggagttcaaaaccatctacatg gccaagaaaccagtgcagctgcccggctattactatgtggacaccaagctg gatatcacatcccacaatgaagactacaccattgtggaacagtatgagagg tctgaaggacgccaccatctgtttctgtacggcatggatgagctgtataag taa.

SEQ ID NO: 3 is amino acid sequence of a mutant tdTomato polypeptide that is a dummy-fluorescent tdTomato polypeptide, that is referred to herein as "tdTomato DM1", "DF tdTomato DM1", "DM1", and "Dummy 1", and that has a Y→A substitution at amino acids corresponding to positions 68 and 310 in SEQ ID NO: 1:

MVSKGEEVIKEFMRFKVRMEGSMNGHEFEIEGEGEGRPYEGTQTAKLKVTK

GGPLPFAWDILSPQFMAGSKAYVKHPADIPDYKKLSFPEGFKWERVMNFED

GGLVTVTQDSSLQDGTLIYKVKMRGTNFPPDGPVMQKKTMGWEASTERLYP

RDGVLKGEIHQALKLKDGGHYLVEFKTIYMAKKPVQLPGYYYVDTKLDITS

HNEDYTIVEQYERSEGRHHLFLGHGTGSTGSGSSGTASSEDNNMAVIKEFM

RFKVRMEGSMNGHEFEIEGEGEGRPYEGTQTAKLKVTKGGPLPFAWDILSP

QFMAGSKAYVKHPADIPDYKKLSFPEGFKWERVMNFEDGGLVTVTQDSSLQ

DGTLIYKVKMIRGTNEPPDGPVMQKKTMGWEASTERLYPRDGVLKGEIHQA

LKLKDGGHYLVEFKTIYMAKKPVQLPGYYYVDTKLDITSHNEDYTIVEQYE

RSEGRHELFLYGMDELYK.

SEQ ID NO: 4 is a mammalian-codon-optimized nucleic acid sequence of mutant tdTomato (referred to herein as "tdTomato DM1", "DF tdTomato DM1", "DM1", and "Dummy 1") that encodes the tdTomato DM1 polypeptide set forth as SEQ ID NO: 3:

atggtgagtaagggcgaggaagtgatcaaagagttcatgcggtttaaggtg agaatggaaggaagcatgaacggccacgagttcgaaattgagggagaagga gagggacggccctacgagggcacccagacagccaagctgaaagtgacaaag ggcgggcctctgccattcgcttgggacatcctgagcccacagtttatggcc ggctccaaggcctatgtgaaacatccagctgacattcccgattataagaaa ctgagcttccccgaggggtttaagtgggaaagagtgatgaacttcgaggac ggaggcctggtgactgtgacccaggacagctccctgcaggatgggaccctg atctacaaggtgaaaatgagagggacaaattttccccctgatggacctgtg atgcagaagaaaactatgggatgggaggcctccaccgaaaggctgtatcca cgcgacggggtgctgaaaggagaaatccaccaggctctgaagctgaaagat gggggacattacctggtggagttcaagacaatctacatggccaagaaacct gtgcagctgccaggctactattacgtggacacaaaaactggatatcacttca cacaacgaggactacactattgtggagcagtatgaacggagcgaggggaga caccatctgttcctgggccatgggactggaagtaccggctcagggtctagt ggaaccgcctcaagcgaggataacaatatggctgtgatcaaagagttcatg aggtttaaggtgcgcatggagggcagcatgaatgggcacgaatttgagatt gaaggagagggcgaagggaggccttacgagggcacacagactgccaagctg aaagtgaccaagggaggaccactgcctttcgcttgggatatcctgtctcct cagtttatggccgaagtaaggcctatgtcaagcatcccgctgacattcct gattacaagaaactgtctttcccagagggctttaagtgggagagagtgatg aattttgaagatggaggcctggtgaccgtgacacaggactcctctctgcag gatggcactctgatctacaaagtcaaaatgcgcggcaccaattttccaccc gatgggcccgtgatgcagaagaaaacaatggggtggggaggccagcactgaa cggctgtatcctagagacggagtgctgaagggcgaaatccaccaggccctg aagctgaaagacggcggccactacctggtggagttcaaaaccatctacatg gccaagaaaccagtgcagctgcccggctattactatgtggacaccaagctg gatatcacatcccacaatgaagactacaccattgtggaacagtatgagagg tctgaaggacgccaccatctgtttctgtacggcatggatgagctgtataag taa.

SEQ ID NO: 5 is amino acid sequence of a mutant tdTomato polypeptide that is a dummy-fluorescent tdTomato polypeptide, that is referred to herein as "tdTomato DM2", "DF tdTomato DM2", "DM2", and "Dummy 2"; and that has a Y→G substitution at amino acids corresponding to positions 68 and 310 in SEQ ID NO: 1:

MVSKGEEVIKEFMRFKVRMEGSMNGHEFEIEGEGEGRPYEGTQTAKLKVTK

GGPLPFAWDILSPQFMGGSKAYVKHPADIPDYKKLSFPEGFKWERVMNFED

GGLVTVTQDSSLQDGTLIYKVKMRGTNFPPDGPVMQKKTMGWEASTERLYP

RDGVLKGEIHQALKLKDGGHYLVEFKTIYMAKKPVQLPGYYYVDTKLDITS

HNEDYTIVEQYERSEGRHHLFLGHGTGSTGSGSSGTASSEDNNMAVIKEFM

RFKVRMEGSMNGHEFEIEGEGEGRPYEGTQTAKLKVTKGGPLPFAWDILSP

QFMGGSKAYVKHPADIPDYKKLSFPEGFKWERVMNFEDGGLVTVTQDSSLQ

DGTLIYKVKMIRGTNEPPDGPVMQKKTMGWEASTERLYPRDGVLKGEIHQA

LKLKDGGHYLVEFKTIYMAKKPVQLPGYYYVDTKLDITSHNEDYTIVEQYE

RSEGRHHLFLYGMDELYK.

SEQ ID NO: 6 is a mammalian-codon-optimized nucleic acid sequence of mutant tdTomato (referred to here as "tdTomato DM2", "DM2", "Dummy 2", and "DF tdTomato DM2) that encodes the tdTomato DM2 polypeptide set forth as SEQ ID NO: 5:

```
atggtgagtaagggcgaggaagtgatcaaagagttcatgcggtttaaggtg
agaatggaaggaagcatgaacggccacgagttcgaaattgagggagaagga
gagggacggccctacgagggcacccagacagccaagctgaaagtgacaaag
ggcgggcctctgccattcgcttgggacatcctgagcccacagtttatggcc
ggctccaaggcctatgtgaaacatccagctgacattcccgattataagaaa
ctgagcttccccgaggggtttaagtgggaaagagtgatgaacttcgaggac
ggaggcctggtgactgtgacccaggacagctccctgcaggatgggaccctg
atctacaaggtgaaaatgagagggacaaattttccccctgatggacctgtg
atgcagaagaaaactatgggatgggaggcctccaccgaaaggctgtatcca
cgcgacggggtgctgaaaggagaaatccaccaggctctgaagctgaaagat
gggggacattacctggtggagttcaagacaatctacatggccaagaaacct
gtgcagctgccaggctactattacgtggacacaaaactggatatcacttca
cacaacgaggactacactattgtggagcagtatgaacggagcgaggggaga
caccatctgttcctgggccatgggactggaagtaccggctcagggtctagt
ggaaccgcctcaagcgaggataacaatatggctgtgatcaaagagttcatg
aggtttaaggtgcgcatggagggcagcatgaatgggcacgaatttgagatt
gaaggagagggcgaaggaggccttacgagggcacacagactgccaagctg
aaagtgaccaagggaggaccactgcctttcgcttgggatatcctgtctcct
cagtttatggcggaagtaaggcctatgtcaagcatcccgctgacattcct
gattacaagaaactgtctttcccagagggctttaagtgggagagagtgatg
aattttgaagatggaggcctggtgaccgtgacacaggactcctctctgcag
gatggcactctgatctacaaagtcaaaatgcgcggcaccaattttccaccc
gatgggcccgtgatgcagaagaaaacaatgggtgggaggccagcactgaa
cggctgtatcctagagacggagtgctgaagggcgaaatccaccaggccctg
aagctgaaagacggcggccactacctggtggagttcaaaaaccatctacatg
gccaagaaaccagtgcagctgcccggctattactatgtggacaccaagctg
gatatcacatcccacaatgaagactacaccattgtggaacagtatgagagg
tctgaaggacgccaccatctgtttctgtacggcatggatgagctgtataag
taa.
```

SEQ ID NO: 7 is a representative amino acid sequence of tdTomato polypeptides with amino acid residues that correspond to the amino acids in SEQ ID NO: 1 at 67, 68, 69, 309, 310, and 311 indicated as: $X_1$, $X_2$, $X_3$, $X_4$, $X_5$, and $X_6$, respectively. In SEQ ID NO: 1, $X_1$ is M, $X_2$ is Y, $X_3$ is G, $X_4$ is M, $X_5$ is Y, and $X_6$ is G. Amino acid substitutions at positions $X_1$, $X_2$, $X_3$, $X_4$, $X_5$, and $X_6$ are shown in Table 1.

MVSKGEEVIKEFMRFKVRMEGSMNGHEFEIEGEGEGRPYEGTQTAKLKVTK
GGPLPFAWDILSPQFX$_1$X$_2$X$_3$SKAYVKHPADIPDYKKLSFPEGFKWERVMNF
EDGGLVTVTQDSSLQDGTLIYKVKMRGTNFPPDGPVMQKKTMGWEASTERL
YPRDGVLKGEIHQALKLKDGGHYLVEFKTIYMAKKPVQLPGYYYVDTKLDI
TSHNEDYTIVEQYERSEGRHHLFLGHGTGSTGSGSSGTASSEDNNMAVIKE
FMRFKVRMEGSMNGHEFEIEGEGEGRPYEGTQTAKLKVTKGGPLPFAWDIL
SPQFX$_4$X$_5$X$_6$KAYVKHPADIPDYKKLSFPEGFKWERVMNFEDGGLVTVTQDS
SLQDGTLIYKVKMRGTNFPPDGPVMQKKTMGWEASTERLYPRDGVLKGEIH
QALKLKDGGHYLVEFKTIYMAKKPVQLPGYYYVDTKLDITSHNEDYTIVEQ
YERSEGRHHLFLYGMDELYK.

SEQ ID NO: 8 is the amino acid sequence of ChrimsonR polypeptide, which is also referred to as "ChR88R":

MAELISSATRSLFAAGGINPWPNPYHHEDMGCGGMTPTGECFSTEWWCDPS
YGLSDAGYGYCFVEATGGYLVVGVEKKQAWLHSRGTPGEKIGAQVCQWIAF
SIAIALLTFYGFSAWKATCGWEEVYVCCVEVLFVTLEIFKEFSSPATVYLS
TGNHAYCLRYFEWLLSCPVILIRLSNLSGLKNDYSKRTMGLIVSCVGMIVF
GMAAGLATDWLKWLLYIVSCIYGGYMYFQAAKCYVEANHSVPKGHCRMVVK
LMAYAYFASWGSYPILWAVGPEGLLKLSPYANSIGHSICDIIAKEFWTFLA
HHLRIKIHEHILIHGDIRKTTKMEIGGEEVEVEEFVEEEDEDTV.

SEQ ID NO: 9 is a mammalian-codon optimized DNA sequence encoding ChR88R light-activated ion channel polypeptide set forth herein as SEQ ID NO: 8:

```
atggctgagctgatcagcagcgccaccagatctctgtttgccgccggaggc
atcaacccttggcctaaccctaccaccacgaggacatgggctgtggagga
atgacacctacaggcgagtgcttcagcaccgagtggtggtgtgaccttct
tacggactgagcgacgccggatacggatattgcttcgtggaggccacaggc
ggctacctggtcgtgggagtggagaagaagcaggcttggctgcacagcaga
ggcacaccaggagaaaagatcggcgcccaggtctgccagtggattgctttc
agcatcgccatcgccctgctgacattctacggcttcagcgcctggaaggcc
acttgcggttgggaggaggtctacgtctgttgcgtcgaggtgctgttcgtg
accctggagatcttcaaggagttcagcagccccgccacagtgtacctgtct
accggcaaccacgcctattgcctgcgctacttcgagtggctgctgtcttgc
ccgtgatcctgatcagactgagcaacctgagcggcctgaagaacgactac
agcaagcggaccatgggcctgatcgtgtcttgcgtgggaatgatcgtgttc
ggcatggccgcaggactggctaccgattggctcaagtggctgctgtatatc
gtgtcttgcatctacggcggctacatgtacttccaggccgccaagtgctac
gtggaagccaaccacagcgtgcctaaaggccattgccgcatggtcgtgaag
ctgatggcctacgcttacttcgcctcttggggcagctacccaatcctctgg
gcagtgggaccagaaggactgctgaagctgagcccttacgccaacagcatc
ggccacagcatctgcgacatcatcgccaaggagttttggaccttcctggcc
caccacctgaggatcaagatccacgagcacatcctgatccacggcgacatc
cggaagaccaccaagatggagatcggaggcgaggaggtggaagtggaagag
ttcgtggaggaggaggacgaggacacagtg.
```

SEQ ID NO: 10 is the DNA sequence of the ER export sequence (also referred to herein as "ER2"): ttctgctacgagaatgaagtg.

SEQ ID NO: 11 is the amino acid sequence of the ER export sequence encoded by SEQ ID NO: 10 and also referred to herein as "ER2": FCYENEV.

SEQ ID NO: 12 is the DNA sequence of KGC, which is a C terminal export sequence from the potassium channel Kir2.1:

aaatccagaattacttctgaaggggagtatatccctctggatcaaatagac
atcaatgtt.

SEQ ID NO: 13 is the amino acid sequence of KGC encoded by SEQ ID NO: 12, which is a C terminal export sequence from the potassium channel Kir2.1:

KSRITSEGEYIPLDQIDINV.

SEQ ID NO: 14 is the DNA sequence of SS, which is a signal peptide that is destined towards the secretory pathway:

(atg)gtcccgtgcacgctgctcctgctgttggcagccgccctggctcga
ctcagacgcgggcc

SEQ ID NO: 15 is the amino acid sequence of SS encoded by SEQ ID NO: 14:

(M)VPCTLLLLLAAALAPTQTRA.

SEQ ID NO: 16 is nucleic acid sequence of synapsin promoter, also referred to herein as "syn":

Ctagactgcagagggccctgcgtatgagtgcaagtgggttttaggaccagg
atgaggcggggtgggggtgcctacctgacgaccgaccccgacccactggac
aagcacccaaccccattcccaaattgcgcatccctatcagagaggggg
aggggaaacaggatgcggcgaggcgcgtgcgcactgccagcttcagcaccg
cggacagtgccttcgccccgcctggcggcgcgcgccaccgccgcctcagc
actgaaggcgcgctgacgtcactcgccggtccccgcaaactcccttccc
ggccaccttggtcgcgtccgcgccgccgccggcccagccggaccgcaccac
gcgaggcgcgagataggggggcacgggcgcgaccatctgcgctgcggcgcc
ggcgactcagcgctgcctcagtctgcggtgggcagcggaggagtcgtgtcg
tgcctgagagcgcagtcgaga.

SEQ ID NO: 17 is nucleic acid sequence of a hemagglutinin: tacccatacgatgttccagattacgct.

SEQ ID NO: 18 is amino acid sequence of the hemagglutinin polypeptide encoded by SEQ ID NO: 17: YPYDVPDYA.

SEQ ID NO: 19 is nucleic acid sequence of Ubi promoter, also referred to herein as "ubi":

gggtgcagcggcctccgcgccgggttttggcgcctccgcgggcgccccc
tcctcacggcgagcgctgccacgtcagacgaagggcgcagcgagcgtcctg
atccttccgcccggacgctcaggacagcggcccgctgctcataagactcgg
ccttagaacccagtatcagcagaaggacattttaggacgggacttgggtg
actctagggcactggttttcttccagagagcggaacaggcgaggaaaagt
agtccttctcggcgattctgcggagggatctccgtggggcggtaacgcc gatgattatataaggacgcgccgggtgtggcacagctagttccgtcgcagc
cgggatttgggtcgcggttcttgtttgtggatcgctgtgatcgtcacttgg
tgagtagcgggctgctgggctggccggggctttcgtggccgccgggccgct
cggtgggacggaagcgtgtggagagaccgccaagggctgtagtctgggtcc
gcgagcaaggttgccctgaactggggtttggggggagcgcagcaaatggc
ggctgttcccgagtcttgaatggaagacgcttgtgaggcgggctgtgaggt
cgttgaaacaaggtgggggcatggtgggcggcaagaacccaaggtcttga
ggccttcgctaatgcgggaaagctcttattcgggtgagatgggctgggca
ccatctgggaccctgacgtgaagtttgtcactgactggagaactcggttt
gtcgtctgttgcggggcggcagttatggcggtgccgttgggcagtgcacc
cgtacctttgggagcgcgcgccctcgtcgtgtcgtgacgtcacccgttctg
ttggcttataatgcagggtggggccacctgccggtaggtgtgcggtaggct
tttctccgtcgcaggacgcagggttcgggcctagggtaggctctcctgaat
cgacaggcgccggacctctggtgagggagggataagtgaggcgtcagttt
ctttggtcggttttatgtacctatcttcttaagtagctgaagctccggttt
tgaactatgcgctcggggttggcgagtgtgttttgtgaagttttttaggca
cctttttgaaatgtaatcatttgggtcaatatgtaattttcagtgttagact
agtaaa.

DETAILED DESCRIPTION

The invention, in part, relates to compositions, pharmaceutical compositions, and molecules that can be used in optogenetic compounds, fusion proteins, and methods used in cells and subjects. The invention in some aspects includes expression of fusion proteins comprising a polypeptide that is a Dummy-fluorescent polypeptide. For example, some aspects of the invention include use of mutated tandem dimer Tomato (tdTomato) polypeptide that is a dummy-fluorescent (DF) tdTomato polypeptide.

In some aspects of the invention, a fusion protein that includes a dummy-fluorescent polypeptide also includes a polypeptide that is of interest to express, for example, in a cell. In some aspects of the invention, a polypeptide of interest to express in a cell is an opsin polypeptide such as a stimulus-activated ion channel polypeptide or a stimulus-activated ion pump polypeptide. In certain aspects of the invention, a molecule of interest to express in a cell is an opsin molecule that is a light-activated ion channel polypeptide or its encoding polynucleotide sequence or a light-activated ion pump polypeptide or its encoding polynucleotide sequence.

In some aspects of the invention a polypeptide of interest may be expressed in a fusion protein that also comprises one or more dummy-fluorescent polypeptides of the invention. The invention, in part, also relates to use of dummy-fluorescent polypeptides in diagnostic methods, assays to assess candidate therapeutic agents, methods of treating diseases and conditions in subjects, and other methods. Methods of the invention, in certain embodiments, comprise expressing at least one fusion protein in a cell and/or in a subject, wherein the fusion protein comprises a dummy-fluorescent polypeptide and a polypeptide of interest. In some embodiments of the invention, a fusion protein comprising a polypeptide of interest and a dummy-fluorescent polypeptide of the invention also comprises one or more of a trafficking polypeptide, a targeting polypeptide, a detectably labeled polypeptide, or other polypeptide. The invention, in part, also relates to methods of treating diseases and conditions in subject that include expressing fusion proteins in cells in a subject, wherein a fusion protein expressed in one or more cells in the subject comprises a dummy-fluorescent polypeptide of the invention and a polypeptide of interest.

The invention, in part, relates to the use of modified (also referred to herein as "mutated") fluorescent polypeptides that retain structure, but do not fluoresce. Non-limiting example of a fluorescent polypeptide and encoding polynucleotide is a red fluorescent polypeptide and its encoding polynucleotides. The invention in part, includes mutated or modified fluorescent polypeptides that have reduced or eliminated levels of fluorescence, and their encoding polynucleotides, which are referred to herein as "dummy-fluorescent" polypeptides and polynucleotides, respectively.

The presence of fluorescent polypeptides in cells has been determined to cause damage or toxicity to the cells due to the fluorescence. Dummy-fluorescent polypeptides of the invention can be expressed in fusion proteins, in cells and subjects, and can be used in optogenetic assays and treatment methods. Because dummy-fluorescent proteins of the invention lack the florescence level of traditional fluorescent proteins, their inclusion in fusion proteins that are expressed in cells, tissues, and subjects reduces or eliminates damage and toxicity compared to that resulting from inclusion of traditional fluorescing fluorescent proteins in the fusion proteins.

Numerous fluorescent polypeptides are known in the art and are used routinely in optogenetic and other molecular biology methods. Examples of fluorescent polypeptides include, but are not limited to: tdTomato, mCherry, red fluorescent protein (RFP), DS-Red monomer, mPlum, mCitrine, J-Red, mOrange, Venus, YPet, Cerulean, Emerald, T-sapphire and functional variants thereof. [see Shaner, N., et al., (2005) Nature Methods, vol. 2, No. 12, 905-909 and supplemental materials, the content of which is incorporated by reference herein in its entirety.] As used herein, the term "functional variant" used in the context of a fluorescent polypeptide or its encoding polynucleotide, means a polypeptide or polynucleotide that differs in sequence from its parent polypeptide or encoding polynucleotide, respectively, but retains all or a significant level of the fluorescence of its parent molecule. Examples of fluorescent polypeptides and fluorescent functional variants thereof and their encoding polynucleotides are known and used in the art.

A non-limiting example of a fluorescent polypeptide is a red fluorescent protein known as: tdTomato. The amino acid sequence of tdTomato and its encoding polynucleotide sequence are provided herein as SEQ ID NOs: 1 and 2, respectively. Non-limiting examples of dummy-fluorescent molecules of the invention are the tdTomato DM1 polypeptide having the amino acid sequence set forth herein as SEQ ID NO: 3 and DF functional variants thereof, and the polynucleotide sequence that encodes SEQ ID NO: 3, which is set forth herein as SEQ ID NO: 4 and DF functional variants thereof. Additional non-limiting examples of dummy-fluorescent molecules are the tdTomato DM2 polypeptide having amino acid sequence set forth herein as SEQ ID NO: 5, and DF functional variants thereof, and the polynucleotide sequence that encodes SEQ ID NO: 5, which is set forth herein as SEQ ID NO: 6, and DF functional variants thereof.

Additional dummy-fluorescent polypeptides that are fluorescent tdTomato polypeptide variants (mutants) comprise a sequence set forth as SEQ ID NO: 7 with amino acid substitutions at positions corresponding to positions indicated as $X_1$, $X_2$, $X_3$, $X_4$, $X_5$ and $X_6$ in SEQ ID NO: 7, which correspond to positions 67, 68, 69, 309, 310, and 311, respectively in SEQ ID NO: 1. Amino acid sequence modifications comprising amino acid substitutions at positions $X_1$, $X_2$, $X_3$, $X_4$, $X_5$, and $X_6$ are shown in Table 1 and may be made in the sequence of a tdTomato polypeptide resulting in a dummy-fluorescent tdTomato polypeptide. It will be understood that a dummy-fluorescent tdTomato polypeptide of the invention may include one or more additional sequence modifications that may not directly impact fluorescence of the resulting polypeptide compared to that of SEQ ID NO: 1. For example, a DF-polypeptide of the invention may include one or more sequence modifications compared to the sequence of SEQ ID NO: 1 wherein the modification(s) alter one or more characteristics other than a fluorescent characteristic, such as but not limited to: a level of expression, longevity, localization, trafficking, etc. In some aspects of the invention, a dummy-fluorescent tdTomato polypeptide may comprise one or more sequence modifications (compared to SEQ ID NO: 1) that alter (increase or decrease) one or more functional characteristics compared to those characteristics of SEQ ID NO: 1. Table 1 shows certain embodiments of substitution combinations for: [$X_1$ and $X_4$], which correspond to amino acid positions 67 and 309, respectively, in SEQ ID NO: 1, and as shown in SEQ ID NO: 7); [$X_2$ and $X_5$], which correspond to amino acid positions 68 and 310, respectively, in SEQ ID NO: 1, and as shown in SEQ ID NO: 7); and [$X_3$ and $X_6$], which correspond to amino acid positions 69 and 311, respectively, in SEQ ID NO: 1, and as shown in SEQ ID NO: 7.

TABLE 1

Lines 1-24 show certain embodiments of combinations of substitutions that may be included in a tdTomato polypeptide resulting in a dummy-fluorescent tdTomato polypeptide of the invention. In addition, amino acids at positions corresponding to residues at $X_1$, $X_2$, $X_3$, $X_4$, $X_5$, and $X_6$ in tdTomato DM, tdTomato DM2, and tdTomato are shown in lines 25-27 of the Table.

| Line Number | $X_1$ and $X_4$ amino acids | $X_2$ and $X_5$ amino acids | $X_3$ and $X_6$ amino acids |
| --- | --- | --- | --- |
| 1  | M | G | G |
| 2  | M | A | G |
| 3  | G | G | G |
| 4  | G | A | G |
| 5  | A | A | G |
| 6  | M | Y | A |
| 7  | M | Y | S |
| 8  | M | L | G |
| 9  | M | V | G |
| 10 | M | I | G |
| 11 | G | L | G |
| 12 | G | I | G |
| 13 | G | V | G |
| 14 | A | L | G |
| 15 | A | V | G |
| 16 | A | I | G |
| 17 | A | M | G |
| 18 | G | M | G |
| 19 | G | S | G |
| 20 | A | S | G |
| 21 | A | T | G |
| 22 | G | T | G |
| 23 | G | C | G |
| 24 | A | C | G |

TABLE 1-continued

Lines 1-24 show certain embodiments of combinations of substitutions that may be included in a tdTomato polypeptide resulting in a dummy-fluorescent tdTomato polypeptide of the invention. In addition, amino acids at positions corresponding to residues at $X_1$, $X_2$, $X_3$, $X_4$, $X_5$, and $X_6$ in tdTomato DM, tdTomato DM2, and tdTomato are shown in lines 25-27 of the Table.

| Line Number | $X_1$ and $X_4$ amino acids | $X_2$ and $X_5$ amino acids | $X_3$ and $X_6$ amino acids |
|---|---|---|---|
| 25: amino acids at the indicated positions in tdTomato DM1 SEQ ID NO: 3 | M | A | G |
| 26: amino acids at the indicated positions in tdTomato DM2 SEQ ID NO: 5 | M | G | G |
| 27: amino acids at the indicated positions in tdTomato SEQ ID NO: 1: | M | Y | G |

As used herein, the term: "dummy-fluorescent" is abbreviated as "DF", and thus a dummy-fluorescent tdTomato polypeptide may also be referred to herein as a DF tdTomato polypeptide, a tdTomato-Dummy, and a dummy-fluorescent tdTomato polypeptide. Similarly, a dummy-fluorescent tdTomato polypeptide encoding polynucleotide may also be referred to herein as: a DF tdTomato polynucleotide, a tdTomato-Dummy, and a dummy-fluorescent tdTomato polynucleotide. In addition, with respect to a fluorescence of a polypeptide or polynucleotide, the term "dummy" is used herein interchangeably with "dummy-fluorescent" and "DF".

Certain embodiments of the invention include dummy-fluorescent tdTomato molecules that are polypeptides in fusion proteins or polynucleotide sequences in vectors that encode fusion proteins. Aspects of the invention include such fusion proteins and vectors that are in cells, including in vitro, in vivo, and ex vivo cells. A fusion protein of the invention may, in some aspects, comprise an opsin polypeptide and one or more of a DF polypeptide, for example, though not intended to be limiting: tdTomato polypeptide set forth as SEQ ID NO: 3 or a DF functional variant thereof; SEQ ID NO: 5 or a DF functional variant thereof, or a tdTomato dummy based on a parent Tomato polypeptide sequence that comprises the substitutions set forth in one of lines 1-25 of Table 1, or a DF functional variant thereof.

A non-limiting example of a light-activated opsin polypeptide that may be used in some embodiments of the invention is a ChrimsonR polypeptide (also referred to herein as ChR88R) and functional variants thereof. The light-activated opsin polypeptide ChR88R (SEQ ID NO: 8) is a variant of the Chrimson polypeptide, referred to as ChR88, which is a channelrhodopsin originally derived from the species *Chlamydomonas noctigama*, see PCT Publication No. PCT/US2012/064665; the content of which is incorporated by reference herein in its entirety.

A plasmid construct may be used in some embodiments of the invention, to deliver and/or express a DF polypeptide fused to a light-activated opsin polypeptide, and the construct may comprise a DF molecule, a light-activated opsin molecule, and one or more of: an AAV-Adeno-associated virus; a trafficking sequence, a signal sequence, an export sequence, a Syn-synapsin promoter, such as but not limited to SEQ ID NO: 16 [see Kugler, S. et al., Gene Therapy 10, 337-347, (2003)]; an HA-hemagglutinin, such as but not limited to SEQ ID NO: 17 [see Niman, H. L. et al., Proc. Natl. Acad. Sci. USA 80:4949-4953 (1983)]; an SS-signal sequence, such as but not limited to SEQ ID NO: 14 [see Chow B. Y. et al., Nature, 463, 98-102 (2010)]; a truncated MHC class I antigen corresponding to amino acid sequence, such as but not limited to SEQ ID NO: 15 [see Chow, X. et al., Nature 463, 98-102 (2010)]; an ER2—Endoplasmic reticulum export signal, such as but not limited to SEQ ID NO: 10 [C-terminus from Kir2.1, see Gradinaru, V. et al., Brain Cell Biol. 36, 129-139 (2008)]. In some aspects of the invention, a Ubi promoter sequence may also be included, such as but not limited to SEQ ID NO: 19 [see Christensen A. H. & Quail P. H. Transgenic Res. 5 (3):213-8, (1996)]. The content of each of the above references is incorporated herein by reference in its entirety.

Non-limiting examples of plasmid constructs of the invention that may be used to deliver and/or express a DF tdTomato polypeptide fused to a light-activated opsin polypeptide of the invention comprise a DF tdTomato molecule of the invention, a light-activated opsin molecule, and one or more of: an AAV-Adeno-associated virus; a Syn-synapsin promoter, a non-limiting example of which is set forth as SEQ ID NO: 16; an HA-hemagglutinin, a non-limiting example of which is set forth as SEQ ID NO: 17, an SS-signal sequence, a non-limiting example of which is SEQ ID NO: 14, a truncated MHC class I antigen corresponding to amino acid sequence, a non-limiting example of which is SEQ ID NO: 15, and an ER2—Endoplasmic reticulum export signal, a non-limiting example of which is SEQ ID NO: 10. Non-limiting examples of constructs that may be used to express a DF tdTomato polypeptide fused to a light-activated opsin polypeptide and that may be included in certain compositions of the invention, and used in certain embodiments of methods of the invention are: an AAV-Syn-ChrimsonR-tdTomato-Dummy 1 construct, and an AAV-Syn-ChrimsonR-tdTomato-Dummy 2 construct, an AAV-Syn-ChrimsonR-tdTomato-Dummy that includes substitutions in tdTomato sequence of SEQ ID NO: 1 as described in one of lines 1-25 of Table 1. A non-limiting example of wild-type tdTomato construct is an AAV-Syn-ChrimsonR-tdTomato virus construct.

As used herein, polypeptide components of a fusion protein, such as, but not limited to: a DF polypeptide, an opsin polypeptide, a targeting polypeptide, a signal polypeptide, a detectable label polypeptide, may be referred to being "fused" to each other. For example, when referring to a DF polypeptide and an opsin that are part of a fusion protein, the DF polypeptide may be referred to as being "fused" to the opsin polypeptide.

In some aspects of the invention, in addition to a DF polypeptide and an opsin polypeptide, a fusion protein may include one or more of a trafficking polypeptide, a signal polypeptide, a targeting polypeptide, and functional variants thereof of the invention. Trafficking polypeptides, export polypeptides, signal polypeptides, targeting polypeptides are known in the art and can be included in a fusion protein to direct the location, (also referred to as: localization), of the expressed polypeptide to a specific cell region of interest such as a membrane etc.

Compositions of the invention may include a DF molecule or a DF functional variant thereof, an opsin molecule, and one or more additional molecules. In some embodiments of the invention, a DF molecule or a DF functional variant thereof is a polypeptide. In certain embodiments of the invention, a DF molecule or a DF functional variant thereof is a polynucleotide with a nucleic acid sequence that encodes a DF molecule or a DF functional variant thereof. A DF polypeptide or DF functional variant thereof may be used in embodiments of the invention that include an opsin that is a stimulus-activated opsin. In some aspects of the invention, a stimulus-activated opsin may be a light-activated opsin and may be a light-activated ion channel polypeptide or a light-activated ion pump polypeptide.

A non-limiting example of an opsin molecule that may be included in a fusion protein or encoding vector (polypeptides and/or polynucleotides), is a channelrhodopsin, halorhodopsin, Archaerhodopsin, or Leptosphaeria rhodopsin polypeptide or encoding polynucleotide, numerous of which are known in the art and used as tools for optical control of membrane potential in cells. Such opsins and their functional variants are routinely expressed in fusion proteins and used in optogenetic methods and compositions. Expression of such an opsin in a cell permits modulation of the cell's membrane potential when the cell is contacted with a suitable light under suitable conditions to activate the opsin. Methods to prepare and express a light-activated opsin in a cell and in a subject are well known in the art, as are methods to select and apply an appropriate wavelength of light to the cell in which the opsin is expressed under suitable conditions to activate the expressed opsin channel or ion pump in the cell. In some aspects of the invention one or more DF polypeptides, or DF functional variants thereof may be expressed in two or more fusion proteins comprising one or more independently selected opsins that are expressed in a cell and/or subject. In certain aspects of the invention different wavelengths of light may be applied to a cell or cells comprising one or more fusion proteins, respectively, in order to activate the independently selected opsins, which may be activated by different wavelengths of light. Methods of adjusting illumination variables are known in the art and representative methods can be found in publications such as: Lin, J., et al., Biophys. J. 2009 Mar. 4; 96(5):1803-14; Wang, H., et al., 2007 Proc Natl Acad Sci USA. 2007 May 8; 104(19):8143-8. Epub 2007 May 1; the contents of each of which is incorporated herein by reference in its entirety. It will be understood that an opsin polypeptide that is activated or inhibited by light or that is activated or inhibited by another stimulation means can be used in aspects of compositions and methods of the invention.

In certain implementations, the invention comprises methods for preparing and using genes encoding light-activated opsins such as light-activated ion channel polypeptides and light-activated ion pumps in vectors that also include a nucleic acid molecule that encodes a DF polypeptide or a DF functional variant thereof. The invention, in part, also includes polynucleotides comprising nucleic acid sequences that encode DF polypeptides and DF functional variants thereof of the invention as well as vectors and constructs that comprise such nucleic acid sequences. In some embodiments, the invention includes expression in cells, tissues, and subjects of polypeptides encoded by the nucleic acid sequences.

Dummy-Fluorescent Sequences and Functional Variants

As used herein the term "dummy-fluorescent" molecule means a DF polypeptide or encoding nucleic acid molecule of the invention or a DF functional variant of a DF polypeptide or encoding nucleic acid molecule of the invention. The term "variant" as used herein in the context of polypeptide molecules and/or polynucleotide molecules, describes a molecule with one or more of the following characteristics: (1) the variant differs in sequence from the molecule of which it is a variant, and may be equivalent in length to its parent sequence, or may be longer or shorter than its parent sequence; (2) the variant is a fragment of its parent molecule and is identical in sequence to the corresponding sequence in the parent molecule; and (3) the variant is a fragment of its parent sequence and differs in sequence from the corresponding sequence in the parent molecule. As used herein, the term "parent" in reference to a sequence means a sequence from which a variant directly originates and from which it is derived. As a non-limiting example, with respect to DF tdTomato sequences of the invention, SEQ ID NO: 1 is considered the parent sequence of at the dummy-tdTomato polypeptides set forth in Table 1. In addition, SEQ ID NO: 3 is a parent sequence for DF tdTomato DM1 DF functional variant sequences of the invention; SEQ ID NO: 5 is a parent sequence for DF tdTomato DM2 DF functional variant sequences of the invention; and the each of the other dummy-tdTomato sequences described in Table 1 are a parent of their DF functional variant sequences.

Additional dummy tdTomato polypeptides are described in Table 1, which indicates positions of substituted amino acids that correspond to positions at 67, 68, 69, 309, 310, and 311 in SEQ ID NO: 1 that are shown in SEQ ID NO: 7 as: $X_1$, $X_2$, $X_3$, $X_4$, $X_5$, and $X_6$, respectively. It will be understood that the dummy-tdTomato polypeptides of the invention that are described in Table 1, lines 1-26 include the sequence set forth as SEQ ID NO:1 with the described substitutions, and DF functional variants thereof. As non-limiting examples, dummy-tdTomato polypeptides of the invention may include the sequence set forth as SEQ ID NO: 1 except with the amino acid "A" in the positions that correspond to residues 67, 68, 109 and 110 of SEQ ID NO: 1 and the amino acid "G" in the positions that correspond to residues 69 and 111; and DF functional variants thereof that include one or more sequence modifications to the sequence set forth as SEQ ID NO: 1 in addition to the A, A, G substitutions described in Table 1, line 5. Other non-limiting examples of dummy-tdTomato polypeptides of the invention may be based on the sequence set forth as SEQ ID NO: 1, except with the amino acid "M" in the positions that correspond to residues 67 and 109 of SEQ ID NO: 1, the amino acid "Y" in the positions that correspond to residues 68 and 110, and the amino acid "A" in the positions that correspond to residues 69 and 111; and DF functional variants thereof that include one or more sequence modifications in sequence set forth as SEQ ID NO: 1 in addition to the M, Y, A substitutions described in Table 1, line 6.

A DF tdTomato polypeptide of the invention may have the amino acid sequence set forth as SEQ ID NO: 3 or 5, a DF polypeptide sequence described in Table 1, or a DF functional variant of the polypeptide set forth as SEQ ID NO: 3, 5, or another of the DF tdTomato polypeptides described in Table 1. As used herein the term "modified" or "modification" in reference to a polypeptide sequence or a polynucleotide sequence refers to a change of 1, 2, 3, 4, 5, 6, 7, 8, 9, 10, 11, 12, 13, 14, 15, 16, 17, 18, 19, 20, 21, 22, 23, 24, 25, or more amino acids or nucleic acids, respectively, in the sequence as compared to the parent amino acid sequence set forth herein as SEQ ID NO: 3, SEQ ID NO: 5, or another of the DF tdTomato polypeptides described in Table 1, or its encoding nucleic acid sequence. As used herein, a sequence change or modification may be one or more of a substitution, deletion, insertion or a combination thereof. For example, though not intended to be limiting: the amino acid sequence of a DF variant DF tdTomato polypeptide may be identical to the DF tdTomato sequence set forth as SEQ ID NO: 3 except that it has one, two, three, four, five, or more amino acid substitutions, deletions, insertions, or combinations thereof.

The invention, in some aspects includes DF polypeptides and DF functional variants thereof, and their encoding nucleic acid molecules, that have one or more substitutions or other modifications from molecules described herein, while retaining at least a portion of the function of the parent molecule of which they are a variant. For example, a DF polypeptide sequence can be modified with one or more substitutions, deletions, insertions, combinations thereof, or other modifications and can be tested using methods described herein for characteristics including, but not limited to: expression, cell localization, expression and activity of an opsin that is co-expressed in a fusion protein with the DF polypeptide variant, and fluorescence level of the expressed DF polypeptide variant, etc. Using routine methods, these and other characteristics of DF variants can be examined in vitro and can also be determined in a cell in which the fusion protein comprising the DF variant and an opsin are expressed.

In some aspects of the invention, a DF functional variant of a DF polypeptide has at least a portion of a non-fluorescence characteristic of a DF polypeptide of which it is a DF variant. Non-limiting examples include a DF functional variant of the sequence set forth as SEQ ID NO: 3, SEQ ID NO: 5, or another DF polypeptide set forth in Table 1 would have at least a portion of a non-fluorescence characteristic of its parent DF polypeptide. It will be understood that the lack of fluorescence of a DF polypeptide of the invention such as SEQ ID NO: 3, SEQ ID NO: 5, or another DF polypeptide described in Table 1 is a loss of function. Thus, for example, though not intended to be limiting, SEQ ID NO: 3 and SEQ ID NO: 5 both have a loss of fluorescence compared to their parent sequence, which is SEQ ID NO: 1. In some embodiments of the invention, a DF functional variant of SEQ ID NO: 3, SEQ ID NO: 5, or another DF tdTomato polypeptide described in Table 1, has an equivalent level of fluorescence as its DF tdTomato parent, (e.g., essentially no fluorescence). In certain embodiments of the invention, a DF functional variant of SEQ ID NO: 3, SEQ ID NO: 5, or another DF tdTomato polypeptides described in Table 1 may have a higher level of fluorescence than its DF tdTomato polypeptide parent, but will have a reduced level of fluorescence compared to that of SEQ ID NO: 1, as measured under the same conditions. In certain aspects of the invention, a DF polypeptide functional variant has a level of fluorescence that one of: less than, the same as, or more than the level of fluorescence of its parent polypeptide if its parent is a DF polypeptide, and the DF polypeptide functional variant will have less than 5%, 10%, 15%, 20%, 25%, 30%, 35%, 40%, 45%, 50%, 55%, 60%, 65%, 70%, 75%, 80%, 85%, 90%, 95%, or 100% (including all integers in the stated range) of a level of fluorescence of a full-fluorescence, original-level-fluorescence, non-reduced fluorescent polypeptide from which the DF polypeptide or its parent was originally derived. For example, the tdTomato polypeptide set forth as SEQ ID NO: 1 is considered to be a "full-fluorescence polypeptide", to have a level of fluorescence that "original-level-fluorescence", and is considered to be a "non-reduced-fluorescence level polypeptide". The amino acid sequence set forth herein as SEQ ID NO: 1 is the parent sequence from which DF polypeptides set forth as SEQ ID NO: 3, SEQ ID NO: 5, and the DF tdTomato polypeptides described in lines 1-25 of Table 1, are referred to has having been originally derived.

A DF functional variant of a DF polypeptide may have the same level, a lower level, or a higher level of fluorescence compared to its parent DF polypeptide. For example, a DF functional variant of SEQ ID NO: 3 measured under the same conditions may have one of the same level, a lower level, or a higher level of fluorescence as SEQ ID NO: 3 under the same conditions, and would have a level of fluorescence that is less than 5%, 10%, 15%, 20%, 25%, 30%, 35%, 40%, 45%, 50%, 55%, 60%, 65%, 70%, 75%, 80%, 85%, 90%, 95%, or 100% (including all integers in the stated range) of a level of fluorescence of SEQ ID NO: 1, which is the full-fluorescence, original-level-fluorescence, non-reduced-fluorescence-level polypeptide when measured under the same conditions.

It will be understood that in some embodiments of the invention, a DF functional variant of a DF polypeptide may have an amino acid sequence that corresponds to the amino acid sequence of its parent polypeptide or a variant thereof, but without 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more amino acids corresponding to the amino acid sequence of its parent polypeptide. For example, though not intended to be limiting: in some embodiments of the invention a DF functional variant has an amino acid sequence that corresponds to the amino acid sequence of SEQ ID NO: 3 or a variant thereof, SEQ ID NO: 5 or a variant thereof, or another DF tdTomato polypeptide described in Table 1, or a variant thereof but without 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more amino acids corresponding to the amino acid sequence of set forth herein as SEQ ID NO: 3, SEQ ID NO: 5, or the other DF tdTomato polypeptide described in Table 1, respectively. In some aspects of the invention, a DF functional variant may be a fragment of its parent DF polypeptide, wherein the fragment has at least 75%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to the region of the amino acid sequence of its parent sequence with which it aligns. For example, though not intended to be limiting, in some embodiments of the invention a functional variant may be a fragment of the polypeptide set forth herein as SEQ ID NO: 3, SEQ ID NO: 5, or another DF tdTomato polypeptide described in Table 1, and the fragment has at least 75%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to the region of the amino acid sequence of SEQ ID NO: 3, 5, or the other DF tdTomato polypeptide described in Table 1, respectively, with which it aligns.

In certain aspects of the invention a DF functional variant of a DF polypeptide may comprise an amino acid sequence set forth as the amino acid sequence of the DF polypeptide's parent polypeptide, or a fragment thereof wherein the DF polypeptide includes one or more additional amino acids compared to its parent. For example, though not intended to be limiting, a DF functional variant may include one or more additional amino acids at the C terminus and/or N terminus that are not present in SEQ ID NO: 3 or a fragment thereof, SEQ ID NO: 5 or a fragment thereof, or another DF tdTomato polypeptide described in Table 1 or a fragment thereof.

In certain aspects, the invention includes compositions and methods comprising a DF tdTomato polypeptide that is a fragment of the DF tdTomato amino acid sequence of SEQ ID NO: 3, SEQ ID NO: 5, or another DF tdTomato polypeptide described in Table 1 or that is greater in length than SEQ ID NO: 3, SEQ ID NO: 5, or the other DF tdTomato polypeptide described in Table 1, and that retains at least a portion of the non-fluorescence "function" of the SEQ ID NO: 3, SEQ ID NO: 5, or the other DF tdTomato polypeptide described in Table 1, respectively, and has a reduced level of fluorescence or zero level of fluorescence compared to the fluorescence level of SEQ ID NO: 1 as determined or measured under the same conditions. A DF functional variant of the DF polypeptide set forth as SEQ ID NO: 3, SEQ ID NO: 5, or another DF tdTomato polypeptide described in Table 1 may be shorter or longer than the sequence of SEQ ID NO: 3, SEQ ID NO: 5, or the other DF tdTomato polypeptide described in Table 1, as set forth herein.

A functional variant polypeptide, for example though not intended to be limiting: a DF functional variant polypeptide (also referred to herein as a DF functional "modified" polypeptide) may include one or more deletions, point mutations, truncations, amino acid substitutions and/or additions of amino acids or non-amino acid moieties. Modifications of a polypeptide of the invention, non-limiting examples of which are DF tdTomato polypeptides set forth as SEQ ID NO: 3, SEQ ID NO: 5, and other DF tdTomato polypeptides described in Table 1, may be made in certain aspects of the invention by modification of the nucleic acid sequence that encodes the polypeptide. Modifications of the molecules of the invention also embrace fusion proteins comprising all or part of the amino acid sequence set forth as SEQ ID NO: 3, SEQ ID NO: 5, a DF tdTomato polypeptide described in Table 1, and DF functional variants thereof. Functional variants of other components of vectors and/or fusion proteins are also envisioned, for example functional variants of ER2, SS, hemagglutinin, syn promoters, Kir2 sequences and other export sequences, signal sequences, trafficking sequences etc. that may be include in vectors or fusion proteins of the invention.

In certain embodiments of the invention a polypeptide variant may be a polypeptide that is modified specifically to alter a feature of the polypeptide that may be, but need not be related to its physiological activity. For example, though not intended to be limiting, one or more amino acid residues may substituted, deleted, altered, or added to a DF polypeptide resulting in a DF variant that has one or more of: increased stability, increased delivery efficiency; less toxicity, etc. in a cell in which it is expressed. In conjunction with teaching provided herein, a skilled artisan can use art-known methods to envision, prepare, and utilize additional DF functional variants of DF polypeptides, including but not limited to those set forth herein as SEQ ID NO: 3, SEQ ID NO:5, and the other DF tdTomato polypeptides described in Table 1 but with one, two, three, four, or more additional amino acid substitutions, deletions, additions, or combinations thereof.

Polypeptides suitable for use in methods of the invention can be synthesized with modifications and/or modifications can be made in a polypeptide by selecting and introducing an amino acid substitution, deletion, alteration, or addition. Modified polypeptides then can be tested for one or more activities [e.g., level of fluorescence; toxicity; accurate conformation, localization, activity of a co-expressed opsin polypeptide; stability; etc.] to determine which modification provides a modified (e.g. variant) polypeptide with the desired properties and function, and to determine if the variant is a DF functional variant.

The skilled artisan will also realize that in some aspects of the invention one or more conservative amino acid substitutions may be made in a DF polypeptide of the invention to provide DF functional variant polypeptides, i.e., a DF variant DF that retains at least a portion of a functional capability of the un-modified polypeptide. As used herein, a "conservative amino acid substitution" refers to an amino acid substitution that does not alter the relative charge or size characteristics of the polypeptide in which the amino acid substitution is made. Conservative substitutions of amino acids may, in some embodiments of the invention, include substitutions made amongst amino acids within the following groups: (a) M, I, L, V; (b) F, Y, W; (c) K, R, H; (d) A, G; (e) S, T; (f) Q, N; and (g) E, D. Polypeptide variants can be prepared according to methods for altering polypeptide sequence and known to one of ordinary skill in the art such. Non-limiting examples of DF functional variants of a DF tdTomato polypeptide of the invention are DF tdTomato polypeptides comprising conservative amino acid substitutions of a DF tdTomato DM1 or DM2 polypeptide set forth herein as SEQ ID NOs: 3 and 5, respectively, and one or more of the other dummy-fluorescent polypeptides described in Table 1.

The invention, in part, includes functional variants of a nucleic acid sequence that encodes a DF polypeptide. For example, though not intended to be limiting, the invention in some embodiments includes functional variants of a nucleic acid sequence that encodes a DF tdTomato polypeptide set forth herein as SEQ ID NO: 3, SEQ ID NO: 5, or another of the dummy-tdTomato polypeptides described in Table 1. A functional variant of a DF nucleic acid sequence has at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% identity to the nucleic acid sequence that encodes the DF functional variant's parent polypeptide, and the nucleic acid sequence of the functional variant encodes a polypeptide that is a DF functional variant of its parent DF polypeptide. In certain embodiments of the invention, a functional variant of a dummy-fluorescent polypeptide-encoding polynucleotide has at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99%, nucleic acid sequence identity to its parent polynucleotide sequence. In a non-limiting example, in certain aspects of the invention, a functional variant of SEQ ID NO: 4 or SEQ ID NO: 6 has at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99%, identity to the nucleic acid sequence that encodes a polypeptide set forth as SEQ ID NO: 3 or SEQ ID NO:5, respectively.

Sequence identity and sequence similarity can be determined using standard techniques known in the art. To determine the percent identity or percent similarity of two amino acid sequences the sequences are aligned for optimal comparison purposes (e.g., gaps may be introduced in the sequence of one protein for optimal alignment with the other protein). The amino acid residues at corresponding amino acid positions are then compared. When a position in one sequence is occupied by the same amino acid residue as the corresponding position in the other sequence, then the molecules have identity/similarity at that position. The percent identity or percent similarity between the two sequences is a function of the number of identical positions shared by the sequences (i.e., % similarity=number of identical positions/total number of positions×100). Determination of identity and similarity can be performed using routine alignment methods and any one of a number of well-known computer algorithms designed and used in the art for such a purpose. Similarly, percent identity and percent similarity of polynucleotide sequences encoding a polypeptide of the invention can be determined using art-known alignment and comparison methods for nucleic acid molecules.

Standard art-known methods can be used to prepare variants of DF polypeptides, such as those set forth as SEQ ID NO: 3 and its encoding nucleic acid sequence, SEQ ID NO: 5 and its encoding nucleic acid sequence, and one or more of the other dummy-fluorescent tdTomato polypeptides described in Table 1 and their encoding nucleic acid sequences. A site or region for introducing an amino acid sequence modification may be predetermined, and the mutation per se need not be predetermined. For example, to optimize the performance of a mutation at a given site, random mutagenesis may be conducted at the target codon or region and the expressed polypeptide screened for the level of desired function or activity. Techniques for making substitution mutations at predetermined sites in DNA having a known sequence are well known, for example, M13 primer mutagenesis and PCR mutagenesis. Variant sequences may in some embodiments of the invention be prepared by site specific mutagenesis of nucleic acids in the DNA encoding a polypeptide of the invention, using cassette or PCR mutagenesis or other techniques known in the art, to produce DNA encoding the polypeptide. In certain embodiments of the invention, activity of variant or fragment of a polynucleotide or polypeptide can be tested by cloning the gene encoding the altered polypeptide into a bacterial or mammalian expression vector, introducing the vector into an appropriate host cell, expressing the altered polypeptide, and testing for a functional capability of the polypeptide as disclosed herein. Additional methods for generating recombinant polypeptides are known in the art may include use of prokaryotic and eukaryotic expression systems including but not limited to bacterial and mammalian expression systems.

It is understood in the art that the codon systems in different organisms can be slightly different, and that therefore where the expression of a given protein from a given organism is desired, the nucleic acid sequence can be modified for expression within that organism. Thus, in some embodiments, a DF polypeptide and/or fusion protein of the invention is encoded by a mammalian-codon-optimized nucleic acid sequence, which may in some embodiments be a human-codon optimized nucleic acid sequence. An aspect of the invention provides a nucleic acid sequence that encodes a fusion protein comprising a DF polypeptide or variant thereof of the invention, and that is optimized for expression with a mammalian cell. In certain aspects of the invention, a nucleic acid sequence is optimized for expression in a human cell.

As used herein, the terms "protein" and "polypeptide" are used interchangeably and thus the term polypeptide may be used to refer to a full-length protein and may also be used to refer to a fragment of a full-length protein, and/or functional variants thereof. As used herein, the terms "polynucleotide" and "nucleic acid sequence" may be used interchangeably and may comprise genetic material including, but not limited to: RNA, DNA, mRNA, cDNA, etc., which may include full length sequences, functional variants, and/or fragments thereof.

Component Molecules of Fusion Protein, Vectors, and Compositions

Molecules that may be included in fusion proteins, vectors, compositions, pharmaceutical compositions of the invention, and can be expressed in cells in methods of the invention, include but are not limited to one or more of: opsin polypeptides, detectable label polypeptides, dummy-fluorescent polypeptides, fluorescent polypeptides, trafficking polypeptides, signal polypeptides, export polypeptides, etc.

Non-limiting examples of detectable label polypeptides, which in certain aspects of the invention may be selected independently of a DF polypeptide of the invention, include: green fluorescent protein (GFP); enhanced green fluorescent protein (EGFP), red fluorescent protein (RFP); yellow fluorescent protein (YFP), tdTomato, mCherry, DsRed, cyan fluorescent protein (CFP); far red fluorescent proteins, etc. In certain aspects of the invention, a fluorescent detectable label polypeptide may be included in addition to one or more DF polypeptides, for example for tracking purposes, testing, assays, etc. Numerous fluorescent proteins and their encoding nucleic acid sequences are known in the art and routine methods can be used to include such sequences in fusion proteins and vectors, respectively, of the invention.

Non-limiting of examples of additional sequences that may be included for expression in a fusion protein of the invention are promoter sequences, trafficking sequences, including, but not limited to one or more of the following sequences or functional variants thereof: a Kir2.1 sequence, a KGC sequence, an ER2 sequence, a Syn-synapsin promoter sequence (see for example, SEQ ID NO: 16); an HA-hemagglutinin sequence, an SS-signal sequence, a truncated MHC class I antigen sequence encoding the amino acid sequence SEQ ID NO: 14). Methods for selecting and using trafficking sequences, signal sequences, export sequences etc. in preparing fusion proteins are known in the art, see for example: Chow, X. et al., Nature 463, 98-102 (2010), Gradinaru, V. et al., Brain Cell Biol. 36, 129-139 (2008); and Kugler, S. et al., Gene Therapy 10, 337-347, (2003). The content of each of the above references is incorporated herein by reference in its entirety. A vector or fusion protein of the invention may also include functional variants of one or more of the additional sequences described herein, such as functional variants of parent molecules including but not limited to: SEQ ID NO: 10, 11, 12, 13, 14, 15, 16, 17, 18, and 19. A functional variant that is included in a vector or a fusion protein of the invention, may have one or more additions, deletions, substitutions, or other modifications to the sequence of its parent sequence and retains a portion, or all, of the function of its parent molecule for which the molecule is included in the vector or fusion protein of the invention. For example, though not intended to be limiting, a functional variant of a syn promoter sequence may include the sequence set forth as SEQ ID NO: 16, but with one or more nucleic acid deletions, additions, substitutions to the sequence, and still retain at least a portion of the function for which the syn promoter parent is included in the vector. In another non-limiting example, a functional variant of an SS molecule set forth as SEQ ID NO: 14 may have the amino acid sequence of SEQ ID NO: 14 but with one or more amino acid deletions, additions, and/or substitutions to the sequence, and still retain at least a portion of the function for which the SS sequence is included in the fusion protein. Those skilled in the art will be able to use routine methods to prepare and test functional variants of trafficking, signal sequences, export sequences, etc. for use in certain embodiments of the invention.

Non-limiting examples of trafficking polypeptides, which may also be referred to herein as "export" polypeptides, that may be used in certain embodiments of the invention include, but are not limited to: SEQ ID NOs: 11 and 13. Non-limiting examples of nucleic acid sequences that encode trafficking polypeptides that may be used in some embodiments of the invention include, but are not limited to:

SEQ ID NOs: 10 and 12. Additional trafficking polypeptides and their encoding nucleic acid sequences are known in the art and routine methods can be used to include and use such sequences in fusion proteins and vectors, respectively, of the invention.

Another molecule that may be included in a composition of the invention and used in methods of the invention is an opsin molecule. As used herein, the term "opsin" means an opsin molecule that when expressed in a cell functions as a membrane channel, an ion pump, or other identified structure, based on its sequence. A non-limiting example of an opsin useful in compositions and methods of the invention is a light-activated opsin. As used herein the term "opsin" may include any opsin having a sequence that is one or more of: a wild-type opsin sequence, a modified opsin sequence, a mutated opsin sequence, a chimeric opsin sequence, a synthetic opsin sequence, a functional fragment of an opsin sequence that may include one or more additions, deletions, substitutions, or other modifications to the sequence of the parent opsin sequence from which the variant sequence originates, and a functional variant of an opsin sequence that may include one or more additions, deletions, substitutions, or other modifications to the sequence of the parent opsin sequence from which the variant sequence originates and retain a portion or all of the function of its parent opsin, non-limiting examples of which are: light-activation, ion channel function, and ion pump function, etc.

Methods of preparing and using opsin molecules and functional variants thereof are well known in the art and such opsins may be used in aspects of the invention. Examples of categories opsin molecules, whose members may be included in compositions of the invention and used in methods of the invention include, but are not limited to light-activated microbial opsins such as halorhodopsins, channelrhodopsins, Archaerhodopsins, and Leptosphaeria rhodopsins, members of each of which are well known in the art. Non-limiting examples of opsins that may be included embodiments of compositions, vectors, and used in methods of the invention are: CoChR, ChR2, ChR88, ChR88R, ChR90, ChR64, ChR86, ChR87, ChR90, Chrimson (also known as ChR88), ChrimsonR (also known as ChR88R), Chronos (also known as ChR90), CsChrimson, ReaChR, GtACR, SwiChRca, iChloC, ChloC, ChIEF, V1C1, ChR2-2A-Halo, VChR1, Halo57, Jaws, Halo (also known as: NpHR), eNpH; R, eNpHR 3.0, Arch, eArch 3.0, ArchT, ArchT 3.0, Mac, Mac 3.0; and functional mutants (also referred to herein as "functional variants" thereof. [see Klapoetke et al. (2014) Nature Methods 11(3), 338-346; for review see: Yizhar, O. et al. (2011) Neuron Vol. 71:9-34; the content of each of which is incorporated by reference herein in its entirety.] Additional opsin polypeptides and their encoding nucleic acid sequences are known in the art and routine methods can be used to include and use such sequences and functional variants thereof in fusion proteins and vectors, respectively, of the invention.

An opsin for expression with a DF polypeptide of the invention can be selected based, at least in part, on knowledge in the art regarding the effect on a cell of activating an opsin expressed in that cell. Selecting a type of opsin to include in a fusion protein of the invention that is expressed in a cell can be based at least in part on the knowledge of opsins and their effect on a cell in which they are expressed, when they are activated. Examples, though not intended to be limiting, include: selecting an opsin for inclusion in a fusion protein of the invention because the opsin it is known to be a light-activated ion channel that is activated by contact with blue light; selecting an opsin for inclusion in a fusion protein of the invention because the opsin is a light-activated proton pump that is activated by red light, etc. It will be understood in the art how to selected and use one or more opsins for use in methods and compositions of the invention. In some embodiments of the invention, an opsin is selected that, when activated with a suitable wavelength of light, alters conduction across a membrane in which it is expressed, and/or alters electrical activity in the cell in which it is expressed.

Delivery of Dummy-Fluorescent Polypeptides

Delivery of a DF molecule to a cell and/or expression of a DF polypeptide in a cell can be done using art-known delivery means. In some embodiments of the invention a DF polypeptide and opsin polypeptide of the invention are included in a fusion protein. It is well known in the art how to prepare and utilize fusion proteins that comprise one or more polypeptide sequences. In certain embodiments of the invention, a fusion protein can be used to deliver a DF polypeptide, such as a DF tdTomato polypeptide or DF functional variant thereof of the invention and one or more other polypeptides to a cell. A fusion protein of the invention can be expressed in a specific cell type, tissue type, organ type, and/or region in a subject, or in vitro, for example in culture, in a slice preparation, etc. Preparation, delivery, and use of a fusion protein and its encoding nucleic acid sequences are well known in the art. Routine methods can be used in conjunction with teaching herein to express a DF polypeptide, and optionally one or more additional polypeptides in a desired cell, tissue, or region in vitro or in a subject.

It is an aspect of the invention to provide a light-activated opsin polypeptide of the invention that is non-toxic, or substantially non-toxic in cells in which it is expressed. In the absence of light, a light-activated opsin polypeptide of the invention does not significantly alter cell health or ongoing electrical activity in the cell in which it is expressed. In some embodiments of the invention, a light-activated opsin polypeptide of the invention is genetically introduced into a cellular membrane, and reagents and methods are provided herein for genetically targeted expression of light-activated opsin polypeptides. Routine genetic procedures can also be used to control parameters of expression, such as but not limited to: the amount of a light-activated opsin polypeptide expressed, the timing of the expression, etc.

Inclusion of a DF polypeptide of the invention in a fusion protein that also comprises a light-activated opsin has now been found to result in less toxicity and cell damage compared to a level of toxicity and damage resulting from expression of a fluorescent polypeptide in such a fusion protein. Compositions and methods of the invention that include a DF polypeptide or a DF functional variant thereof of the invention, can be used in methods to express a light-activated opsin polypeptide in specific cell types, specific cell subtypes, and specific spatial regions within an organism, with less damage and/or toxicity to the cells compared to damage and/or toxicity that occur with expression of the light-activated opsin polypeptide with a fluorescent polypeptide. As a non-limiting example, expressing in a cell a fusion protein comprising: a DF tdTomato DM1 (SEQ ID NO: 3) or DF functional variant thereof, or a DF tdTomato DM2 polypeptide (SEQ ID NO: 5) or DF functional variant thereof; or a dummy-fluorescent tdTomato polypeptide described in Table 1 or DF functional variant thereof and a light-activated opsin, and exposing the cell to a light suitable to activate the opsin, results in less toxicity and/or damage in the cell as compared to a level of toxicity and/or damage in a control cell illuminated under the same conditions. In this non-limiting example, the control cell in which a fusion protein is expressed wherein the fusion protein comprises a tdTomato polypeptide having an amino acid sequence such as that set forth as SEQ ID NO:1 or a fluorescent functional variant thereof and the light-activated opsin, and exposing the cell to a light suitable to activate the opsin under the same conditions as those used with the DF polypeptide fusion protein.

In some embodiments of the invention a reagent for genetically targeted expression of a light-activated opsin polypeptide is a vector that comprises a gene encoding a DF polypeptide or DF functional variant thereof of the invention, and gene encoding an opsin polypeptide. As used herein, the term "vector" refers to a nucleic acid molecule capable of transporting between different genetic environments another nucleic acid to which it has been operatively linked. The term "vector" also refers to a virus or organism that is capable of transporting the nucleic acid molecule. One type of vector is an episome, i.e., a nucleic acid molecule capable of extra-chromosomal replication. Some useful vectors are those capable of autonomous replication and/or expression of nucleic acids to which they are linked. Vectors capable of directing the expression of genes to which they are operatively linked are referred to herein as "expression vectors". Other useful vectors, include, but are not limited to viruses such as lentiviruses, retroviruses, adenoviruses, and phages. Vectors useful in some methods of the invention can genetically insert an opsin polypeptide and a DF polypeptide or DF functional variant thereof of the invention into dividing and non-dividing cells and can insert an opsin polypeptide and a DF polypeptide or DF functional variant thereof of the invention into a cell that is an in vivo, in vitro, or ex vivo cell.

Vectors useful in methods of the invention may include additional sequences including, but not limited to, one or more signal sequences and/or promoter sequences, or a combination thereof. In certain embodiments of the invention, a vector may be a lentivirus, adenovirus, adeno-associated virus, or other vector that comprises a gene encoding an opsin polypeptide and a gene encoding a DF polypeptide or functional fragment thereof of the invention. An adeno-associated virus (AAV) such as AAV8, AAV1, AAV2, AAV4, AAV5, AAV9, are non-limiting examples of vectors that may be used to express a fusion protein of the invention in a cell and/or subject. Expression vectors and methods of their preparation and use are well known in the art. Non-limiting examples of suitable expression vectors and methods for their use are provided herein.

Promoters that may be used in methods and vectors of the invention include, but are not limited to, cell-specific promoters or general promoters. A non-limiting examples promoters that can be used in vectors of the invention are: ubiquitous promoters, such as, but not limited to: CMV, CAG, CBA, and EF1a promoters; and tissue-specific promoters, such as but not limited to: Synapsin (e.g., syn-synapsin, syn), CamKIIa, GFAP, RPE, ALB, TBG, MBP, MCK, TNT, Ubi, and aMHC promoters and functional variants thereof. Methods to select and use ubiquitous promoters and tissue-specific promoters are well known in the art. A non-limiting example of a tissue-specific promoter that can be used to express a light-activated opsin polypeptide in a cell such as a neuron is a synapsin (syn) promoter, which can be used to express an opsin polypeptide and DF polypeptide or functional variant thereof, in embodiments of methods of the invention. Additional tissue-specific promoters and general promoters are well known in the art and, in addition to those provided herein, may be suitable for use in compositions and methods of the invention.

Methods of Using Dummy-Fluorescent Molecules

Dummy-fluorescent polypeptides of the invention, such as, but not limited to: tdTomato DM1 and tdTomato DM2 polypeptides and DF functional variants thereof, are well suited for expression in in cells as a component of a fusion protein that also comprises at least one stimulus-activated opsin polypeptide. Expression of the stimulus-activated opsin, for example, a light-activated opsin in the cell can be used to modulate electrical activity of the cell. Because embodiments of compositions and methods of the invention result in less toxicity and cell damage to cells in which DF polypeptides are expressed (compared to cells in which full or higher fluorescent polypeptides are expressed, as described in more detail above herein), use of DF polypeptides of the invention can improve efficacy of treatment methods in cells and subjects when the methods include a expressing a light-activated opsin and a DF polypeptide of the invention, and activating the light-activated opsin. For example, though not intended to be limiting, expressing in a cell a fusion protein comprising a DF tdTomato DM1 polypeptide or variant thereof of the invention, and a ChR88R light-activated opsin polypeptide and contacting the cell with light suitable to activate the ChR88R light-activated polypeptide, will result in less cell toxicity and/or damage in the cell compared to the toxicity or damage in a control cell in which a fusion protein comprising a fluorescent tdTomato polypeptide and a ChR88R light-activated opsin polypeptide are expressed, and which is contacted with the light under substantially identical conditions to activate the ChR88R light-activated polypeptide.

Cells in which a fusion protein comprising an opsin and a DF polypeptide of the invention is expressed can be contacted with a light under suitable stimulation parameters to activate the opsin, thereby modulating electrical activity in the cell. It will be understood that the type and level of modulation of electrical activity and ion flux in a cell will depend, in part, on the light-activated opsin that is expressed in the cell as part of the fusion protein of the invention. Art-known methods can be used to select suitable stimulation parameters such as type of stimulation, illumination wavelength, intensity, pulse rate, etc. for use with compositions and methods of the invention expressed in cells and membranes. See for example: U.S. Pat. Nos. 8,957,028; 9,309,296; 9,284,353; 9,249,234; 9,101690; PCT Pub. No. WO2013/07123; US Pat. Pub No. 20120214188; US Pat. Pub. No. 20160039902; US Pat. Pub No. 20140223679; Packer, A. M. et al., 2012 Nature Methods December 9(12):1202-1205; and Oron, D. et al., Progress in Brain Research, Chapter 7, Volume 196, 2012, Pages 119-143: the content of each of which is incorporated by references in its entirety herein.

Certain aspects of the invention include methods for modulating one or more characteristics of a cell, such as, but not limited to: electrical activity in a cell and ion flux across a cell membrane. Compositions and methods of the invention can be used in a cell, a plurality of cells (for example in two, three, four, five, or more cells), and/or a subject as a means with which to: modulate ion flux across a membrane of a cell, treat a disease or condition in the cell or subject, identify a candidate agent that when contacted with a cell expressing a fusion protein of the invention modulates electrical activity in the cell, identify a candidate agent that when contacted with a cell expressing a fusion protein of the invention modulates ion flux across a membrane of the cell, etc. In some aspects of the invention, methods and compositions are provided that can be used to detect and assess an effect of activating an opsin polypeptide that is expressed in a cell as part of a fusion protein of the invention. Numerous methods for using one or more light-activated opsin polypeptides expressed in a host cell and/or a host subject are known in the art and the compositions and methods of the invention may be used in conjunction with such methods to enhance selective activation of a cell in which a fusion protein of the invention is expressed.

Working operation of a prototype of this invention has been demonstrated in vitro and in vivo, by genetically expressing a fusion protein comprising an opsin polypeptide and a DF polypeptide or DF functional variant thereof of the invention in cells, illuminating the cells with suitable wavelengths of light to activate the opsin, and demonstrating rapid changes in electrical activity and/or ion flux in the cell in response to the light, as well as rapid release from the changes upon cessation of light. Depending on the particular implementation, methods of the invention that include fusion proteins comprising a light-activated opsin and a DF polypeptide of the invention, allow activation of the opsin when the fusion protein is expressed in a cell, with little or no fluorescence-induced damage to the cell.

Cells and Subjects

A cell used in methods and with sequences of the invention may be an excitable cell or a non-excitable cell. A cell in which a fusion protein comprising a light-activated opsin polypeptide and a DF polypeptide or DF functional variant thereof of the invention may be expressed and may be used in methods of the invention include prokaryotic and eukaryotic cells. Useful cells, cells in which compositions and methods of the invention can be used, include, but are not limited to, vertebrate cells, which in some embodiments of the invention may be mammalian cells. Examples of cells in which a fusion protein comprising an opsin polypeptide and a DF polypeptide or DF functional variant thereof of the invention may be expressed are excitable cells, which includes cells able to produce and respond to electrical signals. Examples of excitable cell types include, but are not limited to neurons, visual system cells, auditory system cells, muscles, cardiac cells, and secretory cells (such as pancreatic cells, adrenal medulla cells, pituitary cells, etc.). A cell in which a fusion protein of the invention is expressed may be a single cell, an isolated cell, a cell that is one of a plurality of cells, a cell that is one in a network of two or more interconnected cells, a cell that is one of two or more cells that are in physical contact with each other, etc.

Non-limiting examples of cells that may be used in methods of the invention include: central nervous system cells, peripheral nervous system cells, neurons, cardiac cells, immune system cells, circulatory system cells, visual system cells, auditory system cells, secretory cells, endocrine cells, brain cells, and muscle cells. In some embodiments, a cell used in conjunction with the invention may be a healthy normal cell, which is not known to have a disease, disorder or abnormal condition. In some embodiments, a cell used in conjunction with methods and compositions of the invention may be an abnormal cell, for example, a cell obtained from a subject diagnosed as having a disorder, disease, or condition, including, but not limited to a degenerative cell, a neurological disease-bearing cell, a cell model of a disease or condition, an injured cell, etc. In some embodiments of the invention, a cell may be a control cell. In some aspects of the invention a cell can be a model cell for a disease or condition.

A fusion protein comprising a light-activated opsin polypeptide and a DF polypeptide or DF functional variant thereof of the invention may be expressed in one or more cells from culture, cells in solution, cells obtained from subjects, and/or cells in a subject (in vivo cells). Light-activated opsin polypeptides expressed in fusion proteins of the invention may be expressed and activated in cultured cells, cultured tissues (e.g., brain slice preparations, etc.), and in living subjects, etc. As used herein, the term "subject" may refer to a: human, non-human primate, cow, horse, pig, sheep, goat, dog, cat, rodent, fly or other host organism. As used herein the term "host" means a subject or cell in which a DF polypeptide and/or fusion protein of the invention is expressed. In some aspects of the invention a host is a vertebrate subject. In certain embodiments of the invention, a host is a mammal. In certain aspects of the invention a host is an invertebrate subject.

Controls and Candidate Compound Testing

Using certain embodiments of compositions and methods of the invention, one or more light-activated opsin polypeptides of the invention can be expressed in conjunction with a DF polypeptide of the invention, and methods to stimulate and/or image the response in the cell to activation of the light-activated opsin polypeptide can be utilized to assess changes in cells, tissues, and subjects in which they are expressed. Some embodiments of the invention include delivery of light-activated opsins to a cell with a DF polypeptide of the invention or DF functional variant thereof, to identify effects of one or more candidate compounds on the cell, tissue, and/or subject in which the light-activated opsin is expressed. Results of testing one or more activities of a light-activated opsin polypeptide of the invention can be advantageously compared to a control.

As used herein a control may be a predetermined value, which can take a variety of forms. It can be a single cut-off value, such as a median or mean. It can be established based upon comparative groups, such as cells or tissues that include the light-activated opsin polypeptide of the invention and are contacted with light, but are not contacted with the candidate compound and the same type of cells or tissues that under the same testing condition are contacted with the candidate compound. Another example of comparative groups may include cells or tissues that have a disorder or condition and groups without the disorder or condition. Another comparative group may be cells from a group with a family history of a disease or condition and cells from a group without such a family history. A predetermined value can be arranged, for example, where a tested population is divided equally (or unequally) into groups based on results of testing. Those skilled in the art are able to select appropriate control groups and values for use in comparative methods of the invention. In certain aspects of the invention, a control is a cell that does not include a fusion protein of the invention and an activity in such a cell can be compared to the activity in a cell that does include a fusion protein of the invention.

As a non-limiting example of use of a light-activated opsin polypeptide to identify a candidate therapeutic agent or compound, a fusion protein comprising light-activated opsin polypeptide and a DF polypeptide or DF functional variant thereof of the invention may be expressed in an excitable cell in culture or in a subject and the excitable cell may be contacted with a light that activates the light-activated opsin polypeptide and with a candidate therapeutic compound. In one embodiment of the invention, a test cell in which a fusion protein comprising a light-activated opsin polypeptide and a DF polypeptide or DF functional variant thereof of the invention is expressed is contacted with a light that depolarizes the cell or otherwise alters ion flux across a membrane in the cell and the cell is also contacted with a candidate compound. The cell, tissue, and/or subject that include the cell can be monitored for the presence or absence of a change that occurs in test conditions versus a control condition. For example, in a cell, an activity modulation in the test cell may be a change in the depolarization of the test cell, a change in a depolarization-mediated cell characteristic in the test cell, a change in ion flux across a membrane of the test cell, each of which can be compared to the activity in control cell, and a change that is different in the test cell compared to the control cell, may indicate that the candidate compound has an effect on the test cell, tissue and/or subject that includes the cell. In some embodiments of the invention, an activity of a cell may be one or more of: an action potential, a pH change, release of a neurotransmitter, etc. and may in some embodiments, include a downstream effect on one or more additional cells, which occurs due to the modulation of an activity in the host cell in which the fusion protein comprising the light-activated opsin and a DF polypeptide or DF functional variant thereof of the invention are expressed. Art-known methods can be used to assess electrical activity and ion flux activity and changes and modulation of such activities upon stimulation and activation of a light-activated opsin polypeptide expressed in a cell, with or without additional contact with a candidate compound.

Candidate-compound identification methods of the invention may be carried out in a cell in a subject or in cultured or in vitro cells. Candidate-compound identification methods of the invention that are performed in a subject, may include expressing a fusion protein comprising a light-activated opsin polypeptide and a DF polypeptide or DF functional variant thereof in a subject, contacting the cell in the subject with a light under suitable conditions to activate the light-activated opsin polypeptide, and administering to the subject a candidate compound. The subject is then monitored to determine whether any change occurs that differs from a control effect in a subject (e.g., one or more of: no DF polypeptide, no candidate compound, etc.). Candidate-compound identification methods of the invention that are performed in vitro may include expressing a fusion protein comprising a light-activated opsin polypeptide and a DF polypeptide or DF functional variant thereof of the invention in a cell, which may or may not be a cultured cell, contacting the cell with a light under suitable conditions to activate the light-activated opsin polypeptide and alter electrical activity in the cell and/or ion flux across a membrane of the cell, and contacting the cell with a candidate compound. The cell is then monitored to determine whether any change occurs that differs from a control effect in a substantially similar cell that is not contacted with the candidate compound. Thus, for example, a cell expressing the light-activated opsin polypeptide can, in the presence of a candidate compound, be contacted with a light appropriate to activate the light-activated opsin polypeptide. Contact of the light-activated opsin polypeptide with the candidate compound may also occur at one or more time points prior to, at the same time as, or subsequent to contact with the light appropriate to activate the light-activated opsin polypeptide. A result of such contact with the candidate compound can be measured and compared to a control value as a determination of the presence or absence of an effect of the candidate compound on an activity in the cell, such, but not limited to: an electrical activity and/or ion flux activity.

Methods of identifying effects of candidate compounds using fusion proteins of the invention may also include additional steps and assays to further characterize an identified activity change in the cell, tissue, or subject when the cell is contacted with suitable light and the candidate compound. In some embodiments of the invention, testing in a cell, tissue, or subject can also include testing one or more cells that each comprise one or more independently selected light-activated opsin polypeptides, such that one, two, three, or more different light-activated opsins polypeptides are expressed in two or more cells that may be in close spatial proximity with each other, may be in physical contact with each other, or may be spatially distant from each other. In some aspects of the invention, at least one, two, three, four, or more of the additional light-activated opsin polypeptides are activated by contact with light having a different wavelength than used to activate other of the additional ion channel opsin polypeptides.

In a non-limiting example of a candidate drug identification method of the invention, cells in which a fusion protein comprising a light-activated opsin polypeptide and DF polypeptide or DF functional variant thereof of the invention are contacted with suitable light, and are depolarized, thus triggering release of a neurotransmitter from the cell, then candidate therapeutic compounds are applied that modulate the response of the cell to depolarization (determined for example using patch clamping methods or other suitable art-known means). These and other methods enable therapeutic compound screening using light to activate the opsin of interest that is localized in the cell body of the cell in which it is expressed.

In some embodiments of the invention, a fusion protein comprising a light-activated opsin polypeptide and DF polypeptide or DF functional variant thereof of the invention can be used in test systems and assays for assessing membrane protein trafficking and physiological function in cells and subjects and the use of use of light-activated opsin to modulate electrical activity of a cell and/or to modulate ion flux across a membrane of the cell. Implementation of fusion proteins in cells, activating light-activated opsin polypeptides by contact with a suitable light and contact parameters, identifying modulation of an activity of a cell such as depolarization, APs, ion flux, hyperpolarization etc. are routinely practiced in the art and in combination with methods and compositions of the invention can be used to identify and test candidate therapeutic agents.

In certain aspects of the invention, a fusion protein comprising a light-activated opsin polypeptide and DF polypeptide or DF functional variant thereof of the invention can be expressed in a cell and/or subject and used to assess or diagnose a disease or condition in the subject.

Methods of Treating

Some aspects of the invention include methods of treating a disorder or condition in a cell, tissue, or subject using fusion protein comprising an opsin and a DF polypeptide or DF functional variant thereof of the invention. Treatment methods of the invention may include administering to a subject in need of such treatment, a therapeutically effective amount of a vector encoding a fusion protein comprising a light-activated opsin polypeptide and a DF polypeptide or DF functional variant thereof of the invention, to treat the disorder. In certain aspects of the invention, a therapeutically effective amount of a cell comprising a fusion protein of the invention may be administered to a subject in a treatment method of the invention. It will be understood that a treatment may be a prophylactic treatment or may be a treatment administered following the diagnosis of a disease or condition. A treatment of the invention may reduce or eliminate one or more symptoms or characteristics of a disorder, disease, or condition or may eliminate the disorder, disease, or condition itself. It will be understood that a treatment of the invention may reduce or eliminate progression of a disease, disorder or condition and may in some instances result in the regression of the disease, disorder, or condition. A treatment need not entirely eliminate the disease, disorder, or condition to be considered to be effective.

In certain aspects of the invention, a means of expressing in a cell of a subject, a fusion protein comprising a DF polypeptide or DF functional variant thereof and an opsin polypeptide in a cell of a subject may comprise one or more of: administering to a cell a vector that encodes a fusion protein comprising the opsin polypeptide and a DF polypeptide or DF functional variant thereof of the invention; administering to a subject a cell in which a fusion protein of the invention is present; and administering a fusion protein (or encoding sequence thereof) of the invention to a subject. Delivery or administration of a fusion protein of the invention may include administration of a pharmaceutical composition that comprises a cell, wherein the cell expresses the opsin polypeptide fused to a DF polypeptide or DF functional variant thereof of the invention. Administration of an opsin and DF polypeptide or DF functional variant thereof of the invention, may, in some aspects of the invention include administration of a pharmaceutical composition comprising a vector, wherein the vector comprises a nucleic acid sequence encoding an opsin polypeptide and a DF polypeptide or DF functional variant thereof of the invention, and wherein the administration of the vector results in expression of a fusion protein comprising the opsin polypeptide and the DF polypeptide or DF functional variant thereof in one or more cells in the subject. In some aspects of the invention, expression of an opsin polypeptide in a cell may be referred to as "increasing" expression of that opsin polypeptide in the cell. It will be understood that in some aspects of the invention, the starting level of expression of the opsin in a cell may be zero and a treatment method of the invention may be used to increase that level to a level above zero. In certain aspects of the invention, for example in a subsequent delivery of a fusion protein of the invention to a cell or plurality of cells in a subject, a level of expression of the opsin in the cell may be greater than zero, with one or more of the opsin polypeptides present in the cell or in a plurality of cells, and a treatment method of the invention may be used to increase the expression level of the opsin polypeptide in the subject.

An effective amount of an opsin and a DF polypeptide or DF functional variant thereof of the invention is an amount that results in expression of the opsin in a cell, in a tissue or subject at a level or amount that is beneficial for the subject. An effective amount may also be determined by assessing physiological effects of administration of a composition of the invention on a cell or subject such as a decrease in symptoms of a disease or condition to be treated, following administration. Other assays will be known to a skilled artisan and can be employed for measuring a level of a response to a treatment of the invention. The amount of a treatment may be varied for example by increasing or decreasing the amount of the opsin polypeptide administered, by changing the therapeutic composition in which the opsin polypeptide is administered, by changing the route of administration, by changing the dosage timing, by changing expression conditions of a fusion protein of the invention, by changing the activation amounts and parameters of an opsin polypeptide of the invention, and so on. An effective amount will vary with the particular condition being treated, the age and physical condition of the subject being treated; the severity of the condition, the duration of the treatment, the nature of the concurrent therapy (if any), the specific route of administration, and the like factors within the knowledge and expertise of a health care practitioner. For example, an effective amount may depend upon the location and number of cells in the subject in which the opsin polypeptide and DF polypeptide or DF functional variant thereof of the invention, is to be expressed. An effective amount may also depend on the location of the tissue to be treated. Factors useful to determine an effective amount of a therapeutic are well known to those of ordinary skill in the art and can be addressed with no more than routine experimentation. It is generally preferred that a maximum dose of a composition to increase the level of the opsin polypeptide, and/or to alter the length or timing of activation of the opsin polypeptide in a subject (alone or in combination with other therapeutic agents) be used, that is, the highest safe dose or amount according to sound medical judgment. It will be understood by those of ordinary skill in the art, however, that a patient, also referred to herein as a subject, may insist upon a lower dose or tolerable dose for medical reasons, psychological reasons or for virtually any other reasons.

An opsin polypeptide and DF polypeptide or DF functional variant thereof of the invention may be administered using art-known methods. The manner and dosage administered may be adjusted by the individual physician, healthcare practitioner, or veterinarian, particularly in the event of any complication. The absolute amount administered will depend upon a variety of factors, including the material selected for administration, whether the administration is in single or multiple doses, and individual subject parameters including age, physical condition, size, weight, and the stage of the disease or condition. These factors are well known to those of ordinary skill in the art and can be addressed with no more than routine experimentation.

Pharmaceutical compositions may be used to deliver a fusion protein comprising an opsin and a DF polypeptide or DF functional variant thereof of the invention. A pharmaceutical composition comprising a fusion protein, vector, or nucleic acid encoding a DF polypeptide of the invention may be administered alone, in combination with each other, and/or in combination with other drug therapies, or other treatment regimens that are administered to subjects. A pharmaceutical composition used in the foregoing methods may contain an effective amount of a therapeutic compound or composition of the invention that will increase the level of a desired opsin polypeptide to a level that produces the desired response in a unit of weight or volume suitable for administration to a subject. In some embodiments of the invention, a pharmaceutical composition of the invention may include a pharmaceutically acceptable carrier. It will be understood that the concept and phrase: "delivering a fusion protein" means that the result of the delivery is presence of the fusion protein. Thus, in some aspects of the invention the delivery of a fusion protein to a cell comprises delivering a nucleic acid that encodes the fusion protein to the cell, and in certain aspects of the invention the delivery of a fusion protein to a cell comprises delivery of the expressed fusion protein into the cell. In each instance, the result produced is the presence of the fusion protein in the cell.

Pharmaceutically acceptable carriers include diluents, fillers, salts, buffers, stabilizers, solubilizers and other materials that are well-known in the art. Exemplary pharmaceutically acceptable carriers are described in U.S. Pat. No. 5,211,657 and others are known by those skilled in the art. In certain embodiments of the invention, such preparations may contain salt, buffering agents, preservatives, compatible carriers, aqueous solutions, water, etc. When used in medicine, the salts may be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

One or more of an opsin polypeptide or encoding polynucleotide thereof of the invention, or a cell or vector comprising a nucleic acid sequence encoding an opsin polypeptide and a DF polypeptide or DF functional variant thereof of the invention, may be administered, for example in a pharmaceutical composition, directly to a tissue. Direct tissue administration may be achieved by direct injection, and such administration may be done once, or alternatively a plurality of times. If administered multiple times, the polypeptides, polynucleotides, cells, and/or vectors may be administered using one route or using different routes. For example, though not intended to be limiting, the first (or first few) administrations may be made directly into the affected tissue while later administrations may be systemic.

A dose of a pharmaceutical composition of the invention that is administered to a subject to increase the level of a desired opsin polypeptide in one or more cells of the subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. The amount and timing of activation of an opsin delivered with a DF polypeptide or DF functional variant thereof of the invention (e.g., light wavelength, pulse length, length of light contact, etc.) that has been administered to a subject can also be adjusted based on efficacy of the treatment in a particular subject. Parameters for illumination and activation of an opsin delivered to a subject using a method of the invention, can be determined using teaching herein in conjunction with art-known methods, without requiring undue experimentation.

Various modes of administration known to the skilled artisan can be used to effectively deliver a pharmaceutical composition to increase the level of an opsin polypeptide in a desired cell in a tissue or body region of a subject. Methods for administering such a composition or pharmaceutical compound of the invention may be topical, intravenous, oral, intracranial, intracavity, intrathecal, intrasynovial, buccal, sublingual, intranasal, transdermal, intravitreal, subcutaneous, intramuscular and/or intradermal administration. The invention is not limited by the particular modes of administration disclosed herein. Standard references in the art (e.g., Remington, The Science and Practice of Pharmacy, 2012, Editor: Allen, Lloyd V., Jr, $22^{nd}$ Edition) provide modes of administration and formulations for delivery of various pharmaceutical preparations and formulations in pharmaceutical carriers. Other protocols which are useful for the administration of a therapeutic compound of the invention will be known to a skilled artisan, in which the dose amount, schedule of administration, sites of administration, mode of administration (e.g., intra-organ) and the like vary from those presented herein.

Administration of a cell or vector to increase expression of an opsin polypeptide in one or more cells in a mammal other than a human; and administration and use of a opsin polypeptide and a DF polypeptide or DF functional variant thereof of the invention, e.g. for testing purposes or veterinary therapeutic purposes, may be carried out under substantially the same conditions as described above. It will be understood that embodiments of the invention are applicable to both human and animals. Thus this invention is intended to be used in husbandry and veterinary medicine as well as in human therapeutics.

Disorders, Diseases and Conditions

DF polypeptides of the invention expressed with opsin polypeptides using compositions and methods of the invention may be used to treat disorders and conditions in subjects. Inclusion of a DF polypeptide instead of a fluorescent polypeptide can enhance efficacy of an expressed light-activated opsin in a cell in which a fusion protein comprising the opsin polypeptide and a DF polypeptide or DF functional variant thereof of the invention is expressed due to a reduction or elimination of cell-damaging effects of fluorescence of the fluorescent polypeptide. A fusion protein comprising a light-activated opsin polypeptide and a DF polypeptide of the invention that is expressed in a cell and contacted with a light that activates the opsin polypeptide, results in less damage to the cell, and is less toxic to the cell, than a fusion protein comprising a light-activated opsin polypeptide and a fluorescent polypeptide that is expressed in a cell and contacted with a light that activates the opsin polypeptide. Thus, methods of the invention to treat a disease or condition in a subject that comprise administering a fusion protein comprising a light-activated opsin polypeptide and a DF polypeptide of the invention, are more effective and result in fewer cell-damaging side effects than prior treatment methods that included administering to a subject a fusion protein comprising the light-activated opsin polypeptide and a fluorescent polypeptide. Embodiments of methods of the invention can be used to treat a disease or condition in a subject, with minimal or no cell toxicity or cell damage due to fluorescence from the fusion protein.

A non-limiting example of a treatment method of the invention includes expressing in a cell in a subject in need of such treatment an effective amount of a fusion protein comprising a ChR88R ion channel polypeptide and a tdTomato DM1 polypeptide, contacting the cell with a light suitable to activate the ChR88R ion channel thereby altering one or more voltage-associated activity of the cell. It will be understood that other DF polypeptides as described herein, including those comprising an opsin other than ChR88R, may be used in the example method set forth, and in other treatment methods. Such methods may be used to treat: blindness, reduced vision, visual impairment, deafness, reduced hearing, and/or impaired hearing in a subject. Disorders and conditions that may be treated using methods of the invention include, but are not limited to: partial or complete vision loss; partial or complete hearing loss; injury; memory loss; memory impairment; psychiatric disorders; brain damage; stroke; degenerative neurological condition, such as, but not limited to: Parkinson's disease and Amyotrophic Lateral Sclerosis (ALS); Alzheimer's disease; cardiac damage; cardiac disease; traumatic brain injury; muscle disease; muscle injury; musculoskeletal disorders; seizures; circulatory system disorders; immune system disorders; etc. In some aspects of the invention, compositions and methods of the invention are used to treat visual system diseases and conditions or to augment normal visual system processes. In certain aspects of the invention, compositions and methods of the invention are used to treat auditory system diseases and conditions or to augment normal auditory processes.

In some embodiments of the invention, a fusion protein comprising a light-activated opsin polypeptide and a DF polypeptide or DF functional variant thereof of the invention is administered to a subject who has a partial or complete vision loss and the cell that expresses the opsin can function as a light-sensitive cell in the visual system, thereby permitting a gain of some or all of the lost visual function in the subject. In certain embodiments of the invention, a fusion protein comprising a light-activated opsin polypeptide and a DF polypeptide or DF functional variant thereof of the invention is administered to a subject who has a partial or complete hearing loss and the cell that expresses the opsin can function as a light-sensitive cell in the auditory system thereby permitting a gain of some or all of the lost auditory function in the subject.

The present invention in some aspects includes preparing nucleic acid sequences and polynucleotide sequences; expressing in cells and membranes polypeptides encoded by the prepared nucleic acid and polynucleotide sequences; illuminating the cells and/or membranes with suitable light, and which results in modulation of electrical activity and or ion flux in the cells and across membranes. The ability to controllably alter one or more of: voltage across membranes; ion flux across members, cell depolarization, cell hyperpolarization using contact of the expressed opsin polypeptide with light has been demonstrated for numerous opsins that can be included in compositions and methods of the invention. The present invention enables expression of an opsin in a cell and activation of that expressed opsin with little or no fluorescence-induced damage or injury to the cell, thus enhancing cell survival and enhancing efficacy of treatments of the invention. Compositions and methods of the invention and their use have broad-ranging applications for drug screening, treatments, and research applications, some of which are describe herein.

EXAMPLES

Example 1

Methods
Immunohistochemistry 50,000 hippocampal neuron cells were plated in 24-well plates per well and cells were infected with 2 µl wild type AAV-Syn-ChrimsonR-tdTomato virus and mutant AAV-Syn-ChrimsonR-tdTomato-Dummy 1 and Dummy 2 viruses accordingly. In some studies, neurons that expressed ChrimsonR without fluorophore were visualized by co-transfection with AAV-Syn-GFP or Fubi-tdTomato. Twenty eight (28) days later, cells were washed with cold PBS and fixed with ice-cold 4% paraformaldehyde for 30 min. Cells were then washed with 0.1M glycine in PBS, and then permeabilized with blocking buffer (4% BSA, 5% goat serum and 0.4% Saponin in PBS) for 30 min. Cells were then incubated in primary antibody (anti-RFP, Rockland Antibodies & Assays, Limerick, Pa.) in blocking buffer for overnight at 4° C. Cells were washed 3 times with PBS/0.1M glycine at 5 min each and incubated in secondary antibody (Goat anti-Chicken 488 preadsorbed, Abcam, Cambridge, Mass.) in blocking buffer for overnight at 4° C. After washed 3 times with PBS/0.1M glycine at 5 min each, cells were incubated in 0.5 ml PBS for imaging.

Imaging

Anti-RFP (GFP channel) and tdTomato fluorescence were imaged with Leica DMI 6000B with a 20× objective using a COMS camera (Hamamatsu Orca Flash 2.8). GFP fluorescence was detected by using DG-4 (Chroma 470/22) and imaged using a filter cube (Chroma, 495 dichroic paired with 500 long pass emission filter) and tdTomato fluorescence were detected by using DG-4 (Semrock 575/15) and imaged using a dichroic (600 LP Chroma) paired with an emission filter (640/50 Chroma).

Whole-Cell Electrophysiology In Vitro

Whole-cell patch clamp recordings were made in voltage clamp mode at −65 mV using Multiclamp 700B amplifier, Digidata 1550A digitizer, and a PC running pClamp (Molecular Devices, Sunnyvale, Calif.). Neurons were transfected 5-6 DIV and patched 14-18 DIV. Neurons were bathed in 31-32° C. Tyrode solution containing 125 mM NaCl, 2 mM KCl, 3 mM $CaCl_2$, 1 mM $MgCl_2$, 10 mM HEPES, 30 mM glucose, 0.01 mM NBQX and 0.01 mM GABAzine, 1 µM tetrodotoxin (TTX, Tocris Bioscience, Bristol, UK), 60-150 µM $CdCl_2$. Borosilicate glass patch pipettes were filled with a solution containing 125 mM CsMe, 8 mM NaCl, 0.1 mM $CaCl_2$, 0.6 mM $MgCl_2$, 1 mM EGTA, 10 mM HEPES, 4 mM Mg-ATP, and 0.4 mM Na-GTP.

Primary Neuron Culture

All procedures involving animals were in accordance with the US National Institutes of Health Guide for the Care and Use of Laboratory Animals and approved by the Massachusetts Institute of Technology Committee on Animal Care. Hippocampal neuron was prepared from postnatal day 0 or 1 Swiss Webster (Taconic, Hudson, N.Y.) mice as previously described [Chow, B. Y., et al., Nature 463, 98-102 (2010); Gradinaru, V. et al., Brain Cell Biol. 36, 129-139 (2008)] but with the following modifications: dissected hippocampal tissue was digested with 50 units of papain (Worthington Biochem Corp, Lakewood, N.J.) for 6-8 min, and the digestion was stopped with ovomucoid trypsin inhibitor (Worthington Biochem Corp.). Cells were plated at a density of 20,000-50,000 per glass coverslip coated with Matrigel (BD Biosciences, San Jose, Calif.). Neurons were seeded in 100 µl plating medium containing MEM (Life Technologies), glucose (33 mM, Sigma), transferrin (0.01%, Sigma), Hepes (10 mM), Glutagro (2 mM, Corning, Corning, N.Y.), Insulin (0.13%, Millipore, Bedford, Mass.), B27 supplement (2%, Gibco), heat inactivated fetal bovine serum (7.5%, Corning). After cell adhesion, additional plating medium was added. AraC (0.002 mM, Sigma) was added when glia density was 50-70%. Neurons were grown at 37° C. and 5% $CO_2$ in a humidified atmosphere.

Results
Immunohistochemistry of Wild Type and Dummy tdTomato

Figure 3A:
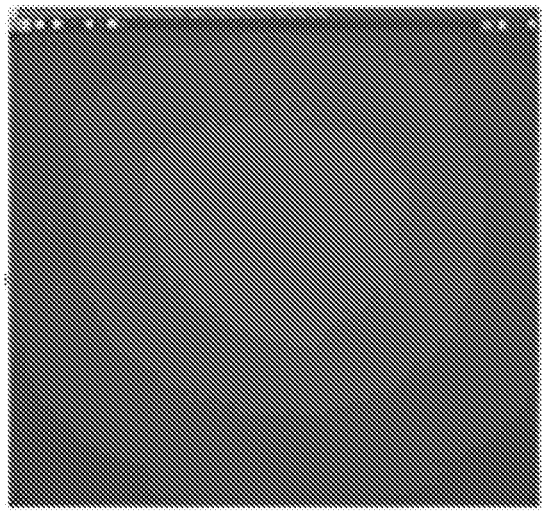
FIG. 3A-F provides photomicrographic images of tdTomato fluorescence as well as immunofluorescence of anti-RFP (GFP channel) in viruses infected neuron cells. Mouse hippocampal neurons were infected with 2 μl wild type AAV-Syn-ChrimsonR-tdTomato virus (FIGS. 3C and 3F), AAV-Syn-ChrimsonR-tdTomato-Dummy 1 (fluorescence dead tdTomato, FIGS. 3A and 3D), and AAV-Syn-ChrimsonR-tdTomato-Dummy 2 (FIGS. 3B and 3E). 28 days later, cells were immune-stained with anti-RFP. Images were taken both in tdTomato channel (FIGS. 3A-C) and GFP channel (FIG. 3D-F).
Figure 3B:
Figure 3C:
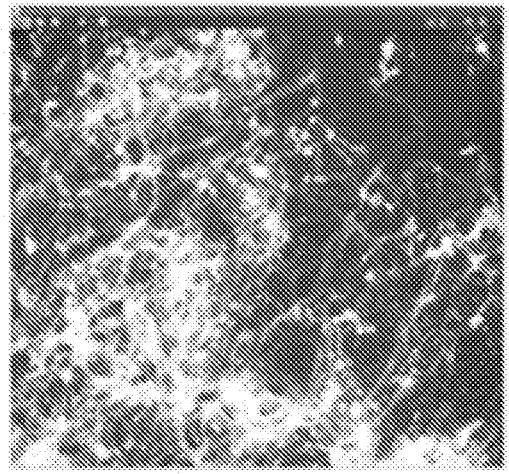
Figure 3D:
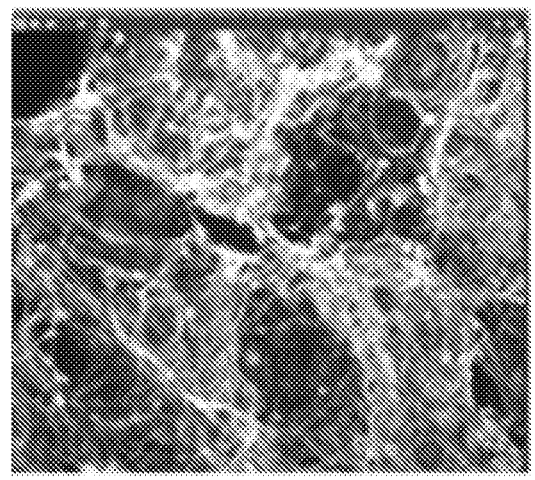
Figure 3E:
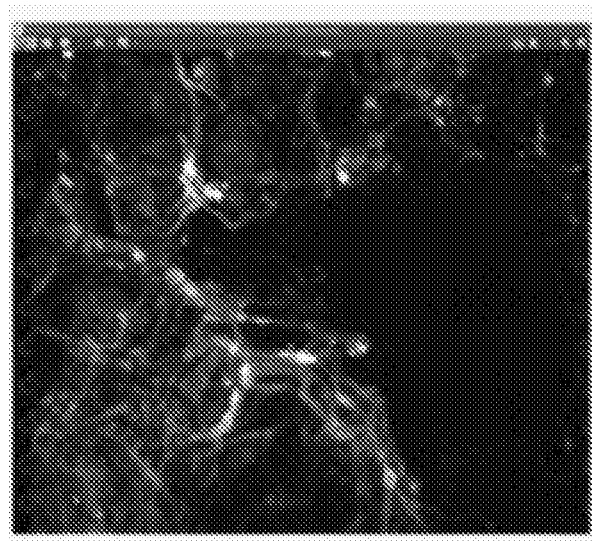
Figure 3F:
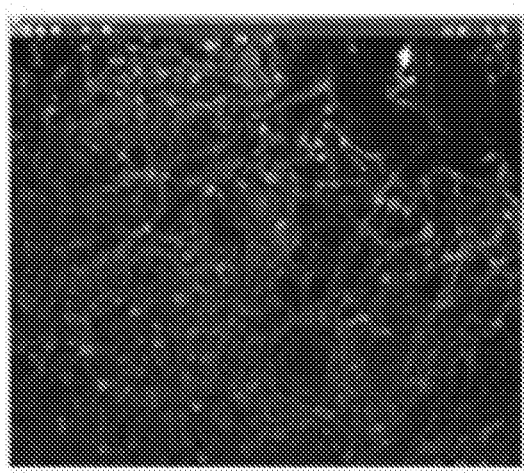

To evaluate the dummy fluorescent tdTomato mutants, mice hippocampal neurons were infected with 2 µl wild type AAV-Syn-ChrimsonR-tdTomato virus (FIGS. 3C and 3F), AAV-Syn-ChrimsonR-tdTomato-Dummy 1 (FIGS. 3A and 3D) and AAV-Syn-ChrimsonR-tdTomato-Dummy 2 (FIGS. 3B and 3E) accordingly. 28 days later, cells were immunostained with anti-RFP. No tdTomato fluorescence was observed in dummy mutants (FIGS. 3A and 3B), however, tdTomato fluorescence was observed in wild-type virus (FIG. 3C). Both wild type (FIG. 3F) and dummy mutants (FIGS. 3D and 3E) could be detected by anti-RFP immunostain.

Electrophysiology Recording

Figure 4A:
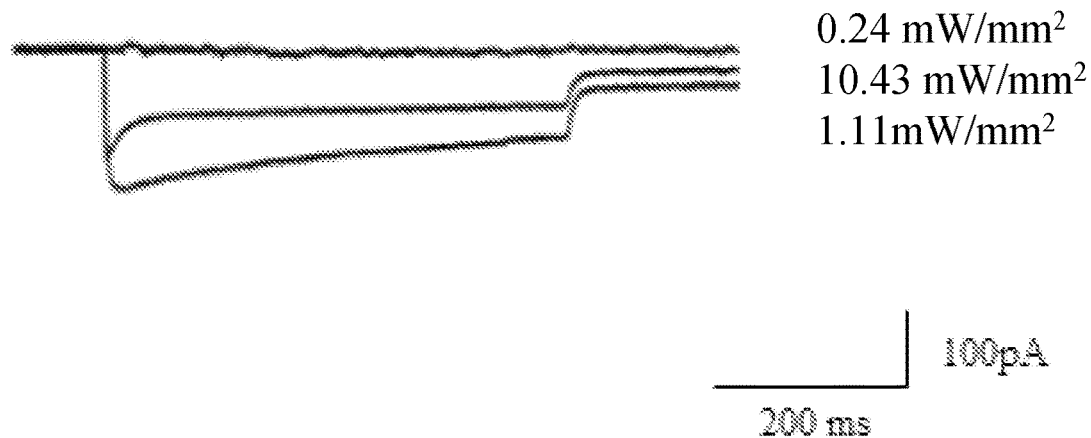
FIG. 4A-C shows photocurrents of ChrimsonR fused to DF tdTomato. Whole-cell currents were recorded in mouse hippocampal neurons expressing ChrimsonR plasmid, which were stimulated with 640±30 nm illumination at three intensity levels: 0.24, 1.11, and 10.43 mW/mm$^2$ at 500 ms.
Figure 4B:
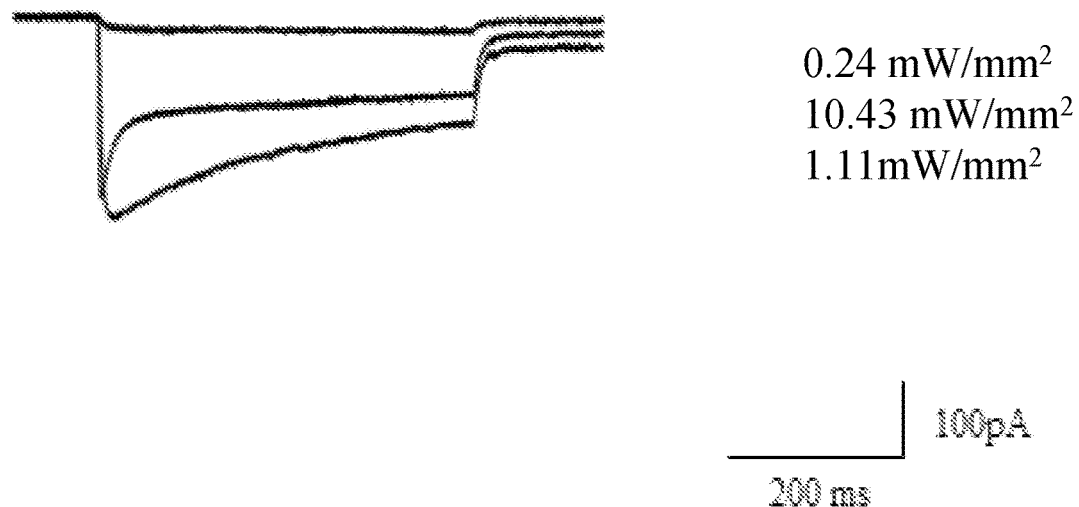
Figure 4C:
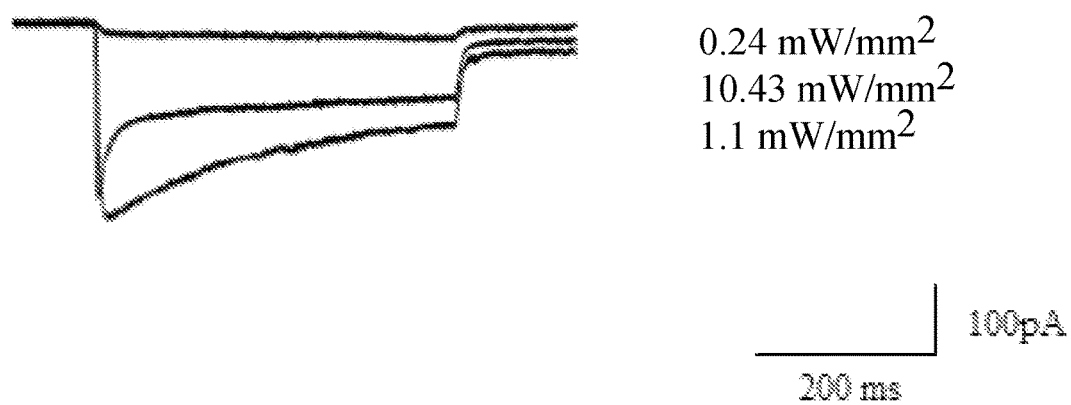
Figure 5A:
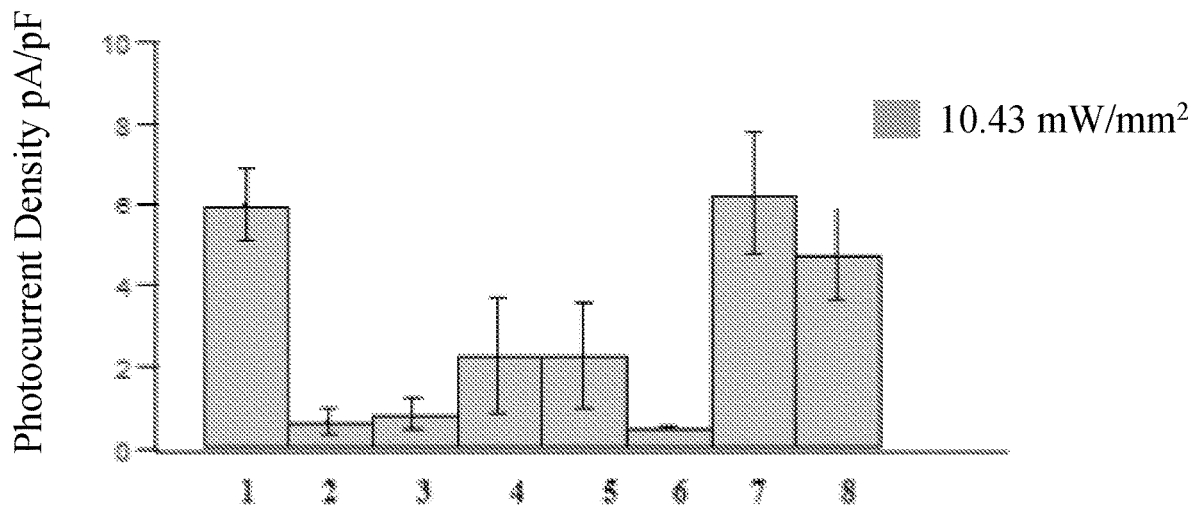

To improve ChrimsonR photocurrent seven (7) additional ChrimsonR plasmid constructs were prepared by: 1) removing tdTomato fluorescent protein, 2) adding trafficking signals, or 3) adding dummy-fluorescent tdTomato (tdTomato dummy) (FIG. 5B), and then photocurrents were measured in cultured hippocampal neurons (FIGS. 4 and 5). Smaller photocurrents were observed in ChrimsonR plasmid variants when tdTomato was removed or adding trafficking signals (absence of tdTomato) compared to the control ChrimsonR (pAAV-Syn-ChrimsonR-tdTomato) (FIGS. 5A and 5C). However, photocurrents of ChrimsonR fused to dummy tdTomato were similar to the control ChrimsonR (FIGS. 4A, 5A, and 5C). Neurons expressing ChrimsonR without fluorophore were visualized by co-transfection with AAV-Syn-GFP or Fubi-tdTomato [Christensen A. H., & Quail P. H. Transgenic Res. 5 (3):213-8, 1996].

Discussion

Long term expression of fluorescent proteins in vivo may cause photobleaching and toxicity, which is a big concern that impedes the clinical use of opsin-fluorescent protein fusions. Experiments have shown the fluorescent protein playing a role in the folding, trafficking and function of the opsin-fluorescent fusion protein. Therefore, studies were performed to identify a means to express ChrimsonR at a high level with low levels of photobleaching and toxicity, for clinical optogenetics.

TdTomato has the X-Tyr-Gly chromophore-forming tripetide and possess a phenol ring derived from the Tyr residue [Miyawaki, A., et al., Current Opinion in Structural Biology 22, 679-688 (2012); Day R. N & Davidson M. W. Chem. Soc. Rev. 38, 2887-2921 (2009]. The Tyr amino acids at positions 68 and 310 of tdTomato polypeptide (for example, SEQ ID NO: 1) were site mutated to either Ala (DM1) or Gly (DM2). The fusion proteins comprising these mutated tdTomato polypeptides and ChrimsonR (ChR88R) were found to exhibit appropriate folding, trafficking, and function. Immunostaining demonstrated that the both of the prepared dummy tdTomato polypeptides showed no detectable tdTomato fluorescence, but the tdTomato polypeptides were still detectible using anti-RFP immuno-stain. Electrophysiology recording of ChrimsonR photocurrent under red light illumination indicated that the dummy tdTomato didn't affect the opsin-fluorescent fusion protein's folding, trafficking and function. In summary, the opsin-dummy tdTomato fusion proteins were prepared, which supports their role in therapeutic optogenetics.

Example 2

Methods and Results

Dummy fluorescent polypeptide molecules are prepared using methods described in Example 1 herein, which may include expression of fusion proteins that include a dummy-fluorescent polypeptide having a tdTomato polypeptide or functional variant as described elsewhere herein, and also a stimulus-activated opsin, for example a light-activated opsin. These fusion proteins may be referred to as tdTomato-opsin fusion proteins. Vectors are prepared that comprise a nucleic acid sequence that encodes the dummy fluorescent polypeptide and a nucleic acid sequence that encodes an opsin polypeptide. Procedures are carried out to prepare fusion proteins that include the opsins ChrimsonR, CoChR, ChR88, Chr90, ChR2, Jaws, Halo, and others described elsewhere herein, or a functional variant of one of the listed opsins. Vectors encoding the dummy fluorescent polypeptide and opsin polypeptide and some also include one or more additional nucleic acid sequences, one or more of which encode an export polypeptide, a trafficking polypeptide, and/or a signal polypeptide. Using standard administration procedures used to deliver vectors to cells and subjects, the prepared vector is administered to a human or animal subject who has a disease or condition, or is at risk of a disease or condition, or is suspected of having a disease or condition that includes abnormal electrical activity in one or more cells or regions in the subject.

The encoded tdTomato-opsin fusion protein is expressed in a cell in the subject in a cell or region with abnormal electrical activity, the cell in which the fusion protein is expressed is contacted with suitable light to activate the expressed opsin and alter the electrical activity of the cell in which it is expressed. The altered electrical activity of the cell reduces the abnormal electrical activity of the cell. A disease in the subject that results from the abnormal electrical activity is treated by contacting the expressed fusion protein with suitable light.

Procedures are performed in which a described vector is administered to a subject having blindness and/or visual impairment that results at least in part from abnormal electrical activity in one or more of a neuronal cell and a visual system cell in the subject. Activation of the opsin that is expressed with the dummy fluorescent polypeptide treats and reduces the blindness in the subject. One or more of the symptoms and/or characteristics of the blindness and/or visual impairment being treated with the procedure are reduced in response to the procedure.

Procedures are performed in which a described vector, prepared using methods set forth in Example 1 is administered to a subject having hearing loss or hearing impairment that results at least in part from abnormal electrical activity in one or more of a neuronal cell and a auditory system cell in the subject. Activation of the opsin that is expressed with the dummy fluorescent polypeptide treats one or more symptoms of hearing loss and/or hearing impairment and increases auditory function in the subject. One or more of the symptoms and/or characteristics of the hearing loss and/or hearing impairment being treated with the procedure are reduced in response to the procedure.

Additional procedures are performed in which a described vector is administered to a subject having a seizure disorder or condition that results at least in part from abnormal electrical activity in one or more of a neuronal cell in the brain of the subject. Activation of the opsin that is expressed with the dummy fluorescent polypeptide treats one or more symptoms of seizure and reduces the seizures in the subject. One or more of the symptoms and/or characteristics of the seizure disorder being treated with the procedure are reduced in response to the procedure.

Procedures are performed in which a described vector is administered to a subject having dementia, memory loss, Parkinson's disease, depression, ALS, and/or Alzheimer's disease symptoms that result at least in part from abnormal electrical activity in one or more of a neuronal cell in the brain in the subject. The opsin that is expressed with the dummy fluorescent polypeptide is contacted with suitable light in an amount effective to decrease the abnormal electrical activity in the patient's cells that include the fusion protein and treat the dementia, memory loss, Alzheimer's disease, depression, Parkinson's disease, and ALS, and to reduce one or more symptoms and/or characteristics of the dementia, memory loss, Alzheimer's disease, depression, and Parkinson's disease in the subject. One or more of the symptoms and/or characteristics of the dementia, memory loss, Alzheimer's disease, depression, ALS, and/or Parkinson's disease being treated with the procedure are reduced in response to the procedure.

Procedures are performed in which a described vector is administered to a subject having a cardiac condition that results at least in part from abnormal electrical activity in one or more of a cardiac cell, a neuronal cell, and a muscle cell in the subject. The opsin that is expressed with the dummy fluorescent polypeptide is contacted with suitable light in an amount effective to reduce the abnormal electrical activity in the patient's cells that include the fusion protein and to treat the cardiac condition and to reduce one or more symptoms and/or characteristics of the cardiac condition in the subject. One or more of the symptoms and/or characteristics of the cardiac condition are reduced in response to the procedure.

Procedures are performed in which a described vector is administered to a subject having an immune system condition that results at least in part from abnormal electrical activity in one or more of an immune system cell in the subject. The opsin that is expressed with the dummy fluorescent polypeptide is contacted with suitable light in an amount effective to reduce the abnormal electrical activity in the patient's cells that include the fusion protein and to treat the immune system condition and to reduce one or more symptoms and/or characteristics of the immune system condition in the subject. One or more of the symptoms and/or characteristics of the immune system condition are reduced in response to the procedure.

Procedures are performed in which a described vector is administered to a subject having a muscle defect, abnormal muscle activity, muscle associated disease or condition that results at least in part from abnormal electrical activity in a muscle cell in the subject or in a cell that stimulates a muscle cell in the subject. The opsin that is expressed with the dummy fluorescent polypeptide is contacted with suitable light in an amount effective to reduce the abnormal electrical activity in the patient's cells that include the fusion protein and to treat the muscle defect, abnormal muscle activity, muscle associated disease or condition and to reduce one or more symptoms and/or characteristics of the muscle defect, abnormal muscle activity, muscle associated disease or condition that results from abnormal electrical activity in cells in the subject. One or more of the symptoms and/or characteristics of the muscle defect, abnormal muscle activity, muscle associated disease or condition that results from abnormal electrical activity in cells in the subject are reduced in response to the procedure.

EQUIVALENTS

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated by reference in their entirety herein.

What is claimed is:

1. A composition comprising a dummy-fluorescent (DF) polypeptide or DF functional variant thereof and a stimulus-activated opsin polypeptide, wherein (i) the amino acid sequence of the DF polypeptide comprises SEQ ID NO: 3, SEQ ID NO: 5, or one of SEQ ID NO: 7, wherein SEQ ID NO: 7 amino acid positons:

67 and 309 are M, 68, 69, 310, and 311 are G;
67 and 309 are M, 68 and 310 are A, and 69 and 311 are G;
67-69 and 309-311 are G;
67 and 309 are G, 68 and 310 are A, and 69 and 311 are G;
67 and 309 are A, 68 and 310 are A, and 69 and 311 are G;
67 and 309 are M, 68 and 310 are Y, and 69 and 311 are A;
67 and 309 are M, 68 and 310 are Y, and 69 and 311 are S;
67 and 309 are M, 68 and 310 are L, and 69 and 311 are G;
67 and 309 are M, 68 and 310 are V, and 69 and 311 are G;
67 and 309 are M, 68 and 310 are I, and 69 and 311 are G;
67 and 309 are G, 68 and 310 are L, and 69 and 311 are G;
67 and 309 are G, 68 and 310 are I, and 69 and 311 are G;
67 and 309 are G, 68 and 310 are V, and 69 and 311 are G;
67 and 309 are A, 68 and 310 are L, and 69 and 311 are G;
67 and 309 are A, 68 and 310 are V, and 69 and 311 are G;
67 and 309 are A, 68 and 310 are I, and 69 and 311 are G;
67 and 309 are A, 68 and 310 are M, and 69 and 311 are G;
67 and 309 are G, 68 and 310 are M, and 69 and 311 are G;
67 and 309 are G, 68 and 310 are S, and 69 and 311 are G;
67 and 309 are A, 68 and 310 are S, and 69 and 311 are G;
67 and 309 are A, 68 and 310 are T, and 69 and 311 are G;
67 and 309 are G, 68 and 310 are T, and 69 and 311 are G;
67 and 309 are G, 68 and 310 are C, and 69 and 311 are G; or
67 and 309 are A, 68 and 310 are C, and 69 and 311 are G;

and (ii) the amino acid sequence of the DF functional variant polypeptide has at least 95% sequence identity to SEQ ID NO: 3, SEQ ID NO: 5, or one of SEQ ID NO: 7, wherein SEQ ID NO: 7 amino acid positions:

67 and 309 are M, 68, 69, 310, and 311 are G;
67 and 309 are M, 68 and 310 are A, and 69 and 311 are G;
67-69 and 309-311 are G;
67 and 309 are G, 68 and 310 are A, and 69 and 311 are G;
67 and 309 are A, 68 and 310 are A, and 69 and 311 are G;
67 and 309 are M, 68 and 310 are Y, and 69 and 311 are A;
67 and 309 are M, 68 and 310 are Y, and 69 and 311 are S;
67 and 309 are M, 68 and 310 are L, and 69 and 311 are G;
67 and 309 are M, 68 and 310 are V, and 69 and 311 are G;
67 and 309 are M, 68 and 310 are I, and 69 and 311 are G;
67 and 309 are G, 68 and 310 are L, and 69 and 311 are G;
67 and 309 are G, 68 and 310 are I, and 69 and 311 are G;
67 and 309 are G, 68 and 310 are V, and 69 and 311 are G;
67 and 309 are A, 68 and 310 are L, and 69 and 311 are G;
67 and 309 are A, 68 and 310 are V, and 69 and 311 are G;
67 and 309 are A, 68 and 310 are I, and 69 and 311 are G;
67 and 309 are A, 68 and 310 are M, and 69 and 311 are G;

67 and 309 are G, 68 and 310 are M, and 69 and 311 are G;
67 and 309 are G, 68 and 310 are S, and 69 and 311 are G;
67 and 309 are A, 68 and 310 are S, and 69 and 311 are G;
67 and 309 are A, 68 and 310 are T, and 69 and 311 are G;
67 and 309 are G, 68 and 310 are T, and 69 and 311 are G;
67 and 309 are G, 68 and 310 are C, and 69 and 311 are G; or
67 and 309 are A, 68 and 310 are C, and 69 and 311 are G.

2. The composition of claim 1, wherein the stimulus-activated opsin is a light-activated opsin polypeptide.

3. The composition of claim 1, wherein the composition is a fusion protein comprising one or more of the DF polypeptide or DF functional variant thereof, the stimulus-activated opsin polypeptide, and one or more of a trafficking polypeptide and a signal polypeptide.

4. A cell comprising the composition of claim 1, wherein the cell is a vertebrate cell.

5. The composition of claim 1, wherein the stimulus-activated opsin polypeptide is a ChrimsonR (ChR88R) polypeptide.

6. A fusion protein comprising a dummy-fluorescent (DF) polypeptide or DF functional variant thereof, wherein (i) the amino acid sequence of the DF polypeptide comprises SEQ ID NO: 3, SEQ ID NO: 5, or one of SEQ ID NO: 7, wherein SEQ ID NO: 7 amino acid positions:
67 and 309 are M, 68, 69, 310, and 311 are G;
67 and 309 are M, 68 and 310 are A, and 69 and 311 are G;
67-69 and 309-311 are G;
67 and 309 are G, 68 and 310 are A, and 69 and 311 are G;
67 and 309 are A, 68 and 310 are A, and 69 and 311 are G;
67 and 309 are M, 68 and 310 are Y, and 69 and 311 are A;
67 and 309 are M, 68 and 310 are Y, and 69 and 311 are S;
67 and 309 are M, 68 and 310 are L, and 69 and 311 are G;
67 and 309 are M, 68 and 310 are V, and 69 and 311 are G;
67 and 309 are M, 68 and 310 are I, and 69 and 311 are G;
67 and 309 are G, 68 and 310 are L, and 69 and 311 are G;
67 and 309 are G, 68 and 310 are I, and 69 and 311 are G;
67 and 309 are G, 68 and 310 are V, and 69 and 311 are G;
67 and 309 are A, 68 and 310 are L, and 69 and 311 are G;
67 and 309 are A, 68 and 310 are V, and 69 and 311 are G;
67 and 309 are A, 68 and 310 are I, and 69 and 311 are G;
67 and 309 are A, 68 and 310 are M, and 69 and 311 are G;
67 and 309 are G, 68 and 310 are M, and 69 and 311 are G;
67 and 309 are G, 68 and 310 are S, and 69 and 311 are G;
67 and 309 are A, 68 and 310 are S, and 69 and 311 are G;
67 and 309 are A, 68 and 310 are T, and 69 and 311 are G;
67 and 309 are G, 68 and 310 are T, and 69 and 311 are G;
67 and 309 are G, 68 and 310 are C, and 69 and 311 are G; or
67 and 309 are A, 68 and 310 are C, and 69 and 311 are G; and (ii) the amino acid sequence of the DF functional variant polypeptide has at least 95% sequence identity to SEQ ID NO: 3, SEQ ID NO: 5, or one of SEQ ID NO: 7, wherein SEQ ID NO: 7 amino acid positions:
67 and 309 are M, 68, 69, 310, and 311 are G;
67 and 309 are M, 68 and 310 are A, and 69 and 311 are G;
67-69 and 309-311 are G;
67 and 309 are G, 68 and 310 are A, and 69 and 311 are G;
67 and 309 are A, 68 and 310 are A, and 69 and 311 are G;
67 and 309 are M, 68 and 310 are Y, and 69 and 311 are A;
67 and 309 are M, 68 and 310 are Y, and 69 and 311 are S;
67 and 309 are M, 68 and 310 are L, and 69 and 311 are G;
67 and 309 are M, 68 and 310 are V, and 69 and 311 are G;
67 and 309 are M, 68 and 310 are I, and 69 and 311 are G;
67 and 309 are G, 68 and 310 are L, and 69 and 311 are G;
67 and 309 are G, 68 and 310 are I, and 69 and 311 are G;
67 and 309 are G, 68 and 310 are V, and 69 and 311 are G;
67 and 309 are A, 68 and 310 are L, and 69 and 311 are G;
67 and 309 are A, 68 and 310 are V, and 69 and 311 are G;
67 and 309 are A, 68 and 310 are I, and 69 and 311 are G;
67 and 309 are A, 68 and 310 are M, and 69 and 311 are G;
67 and 309 are G, 68 and 310 are M, and 69 and 311 are G;
67 and 309 are G, 68 and 310 are S, and 69 and 311 are G;
67 and 309 are A, 68 and 310 are S, and 69 and 311 are G;
67 and 309 are A, 68 and 310 are T, and 69 and 311 are G;
67 and 309 are G, 68 and 310 are T, and 69 and 311 are G;
67 and 309 are G, 68 and 310 are C, and 69 and 311 are G; or
67 and 309 are A, 68 and 310 are C, and 69 and 311 are G.

7. The fusion protein of claim 6, further comprising a stimulus-activated opsin polypeptide.

8. The fusion protein of claim 7, wherein the stimulus-activated opsin is a light-activated opsin and the activating stimulus comprises one or more wavelengths of light.

9. The fusion protein of claim 7, wherein the stimulus-activated opsin polypeptide is a ChrimsonR (ChR88R) polypeptide.

10. The fusion protein of claim 7, further comprising a detectable label.

11. A cell comprising the fusion protein of claim 7, wherein the cell is a vertebrate cell.

12. A cell comprising the fusion protein of claim 7, wherein the cell is a mammalian cell.

13. A cell comprising the composition of claim 1, wherein the cell is a mammalian cell.

\* \* \* \* \*

UNITED STATES PATENT AND TRADEMARK OFFICE
CERTIFICATE OF CORRECTION

PATENT NO. : 11,278,633 B2
APPLICATION NO. : 16/318428
DATED : March 22, 2022
INVENTOR(S) : Yang et al.

Page 1 of 1

It is certified that error appears in the above-identified patent and that said Letters Patent is hereby corrected as shown below:

In the Specification

In Column 1, Lines 11-17, delete:
"This invention was made with government support under R24-MH106075, R01-NS087950, DP2-OD002002-01, DMS-0848804, R01-DA029639-04, R01-NS075421-04, R01-DA029639-05, DPI-NS087724, and sub-award agreement no. 3024 Rehabilitation Institute of Chicago; each awarded by the National Institutes of Health. The government has certain rights in the invention."

And insert:
-- This invention was made with government support under GM104948, R24 MH106075, R01 NS087950, OD002002, R01 DA029639, R01 NS075421, NS087724, and R01 MH103910 awarded by the National Institutes of Health, and DMS0848804 awarded by the National Science Foundation. The government has certain rights in the invention. --

Signed and Sealed this
Twenty-fifth Day of November, 2025

John A. Squires
*Director of the United States Patent and Trademark Office*